US011129594B2

(12) United States Patent
Sendai

(10) Patent No.: US 11,129,594 B2
(45) Date of Patent: Sep. 28, 2021

(54) HARDNESS DERIVING DEVICE, MEDICAL IMAGING SYSTEM, HARDNESS DERIVING METHOD AND HARDNESS DERIVING PROGRAM STORAGE MEDIUM

(71) Applicant: FUJIFILM CORPORATION, Tokyo (JP)

(72) Inventor: Tomonari Sendai, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 1076 days.

(21) Appl. No.: 15/450,051

(22) Filed: Mar. 6, 2017

(65) Prior Publication Data
US 2017/0281131 A1    Oct. 5, 2017

(30) Foreign Application Priority Data

Mar. 30, 2016  (JP) .............................. JP2016-069187

(51) Int. Cl.
A61B 8/00   (2006.01)
A61B 8/08   (2006.01)
A61B 6/00   (2006.01)

(52) U.S. Cl.
CPC .............. A61B 8/485 (2013.01); A61B 6/502 (2013.01); A61B 8/0825 (2013.01); A61B 8/403 (2013.01); A61B 8/4416 (2013.01); A61B 8/461 (2013.01); A61B 8/5223 (2013.01);
(Continued)

(58) Field of Classification Search
None
See application file for complete search history.

(56) References Cited

U.S. PATENT DOCUMENTS 6,587,540 B1* 7/2003 Johnson ............... A61B 5/4312
378/4
2007/0112267 A1* 5/2007 Matsumura ......... G01S 15/8977
600/437
2009/0124903 A1  5/2009 Osaka
(Continued)

FOREIGN PATENT DOCUMENTS

JP    2009-028381 A    2/2009
JP    2011-50625 A     3/2011
(Continued)

OTHER PUBLICATIONS

English language translation of the following: Office action dated Mar. 12, 2019 from the JPO in a Japanese patent application No. 2016-069187 corresponding to the instant patent application.
(Continued)

Primary Examiner — Joel F Brutus
(74) Attorney, Agent, or Firm — Solaris Intellectual Property Group, PLLC

(57) ABSTRACT

A hardness deriving device includes: an acquisition section configured to acquire plural ultrasound images obtained by ultrasound imaging a breast in a state in which the breast is pressed by a pressing member at a plurality of different pressures; and a deriving section configured to find an amount of change at corresponding points between the plural ultrasound images acquired by the acquisition section, and to derive information indicating a hardness of tissue of the breast based on the amount of change at the corresponding points.

15 Claims, 15 Drawing Sheets

(52) U.S. Cl.
CPC ............ *A61B 8/5261* (2013.01); *A61B 8/469* (2013.01); *A61B 8/54* (2013.01)

(56) References Cited

U.S. PATENT DOCUMENTS

| | | | | |
|---|---|---|---|---|
| 2009/0177084 | A1* | 7/2009 | Matsumura | A61B 5/415 600/438 |
| 2010/0030078 | A1* | 2/2010 | Mikami | A61B 6/4417 600/443 |
| 2010/0331694 | A1* | 12/2010 | Waki | A61B 8/08 600/443 |
| 2012/0014588 | A1 | 1/2012 | Chono | |
| 2015/0005633 | A1* | 1/2015 | Kanayama | A61B 8/485 600/438 |
| 2015/0146855 | A1* | 5/2015 | Futamura | G06T 7/0012 378/63 |
| 2015/0272545 | A1 | 10/2015 | Atsuchi | |

FOREIGN PATENT DOCUMENTS

| | | |
|---|---|---|
| JP | 2011-167330 A | 9/2011 |
| JP | 2011-167331 A | 9/2011 |
| JP | 2012-086002 A | 5/2012 |
| JP | 2013-530394 A | 7/2013 |
| JP | 2015-181767 A | 10/2015 |
| WO | 2006/054635 A1 | 5/2006 |
| WO | 2010/116965 A1 | 10/2010 |
| WO | 2014207605 A1 | 12/2014 |

OTHER PUBLICATIONS

English language translation of the following: Office action dated Dec. 17, 2019, from the JPO in a Japanese patent application No. 2019-022078 corresponding to the instant patent application.

English language translation of the following: Office action dated Dec. 11, 2018 from the JPO in a Japanese patent application No. 2016-069187 corresponding to the instant patent application. This office action translation is submitted now in order to supplement the understanding of the cited reference which is being disclosed in the instant Information Disclosure Statement.

* cited by examiner

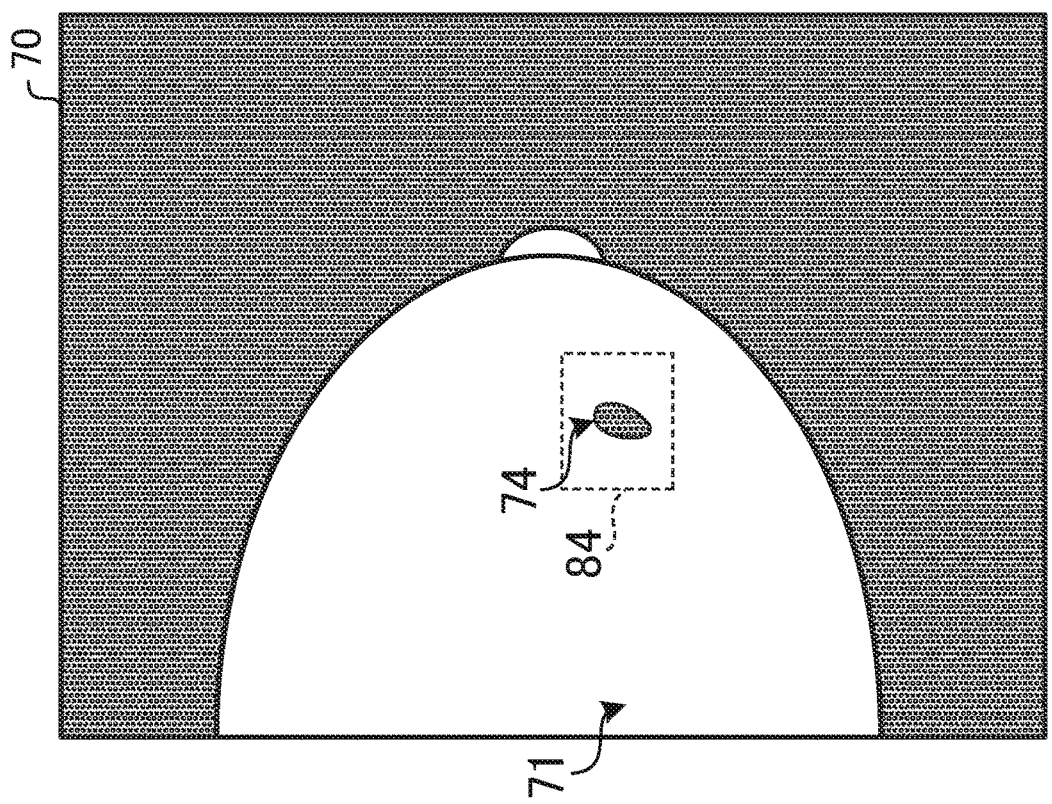

HARDNESS DERIVING DEVICE, MEDICAL IMAGING SYSTEM, HARDNESS DERIVING METHOD AND HARDNESS DERIVING PROGRAM STORAGE MEDIUM

CROSS-REFERENCE TO RELATED APPLICATION

This application claims priority under 35 USC 119 from Japanese Patent Application No. 2016-069187 filed on Mar. 30, 2016, the disclosure of which is incorporated herein by reference in its entirety.

BACKGROUND

Technical Field

The present disclosure relates to a hardness deriving device, a medical imaging system, a hardness deriving method, and a storage medium stored with a hardness deriving program.

Related Art

Ultrasound imaging devices for use in diagnosis and observation of breast tissue are known that perform ultrasound imaging of a breast by scanning the breast with ultrasound waves. Elastography is known as technology to detect the hardness of breast tissue using such ultrasound images.

Generally, when ultrasound images of a breast are imaged with an ultrasound imaging device, an operator moves an ultrasound probe over the surface of the breast of a subject, and performs imaging while pressing the breast with the ultrasound probe.

In elastography the degree of pressing of the breast generally differs according to the operator and the skill of the operator, such that consistent detection results for elastography, namely detection results for breast hardness, may not be obtained.

As technology for elastography not influenced by the operator, automatic elastography technology is described in Japanese National Phase Application Publication No. 2013-530394, in which elastographic images are imaged by scanning a breast with an ultrasound probe while the breast is in a state lightly pressed by a paddle.

However, although the technology described in the above document enables elastography to be performed with the breast in a lightly pressed state, with the degree of pressing of the breast uniform irrespective of the operator, in order to detect the relative hardness of breast tissue in this technology, there is a desire for technology that enables consistent measurement of the hardness of breast tissue.

SUMMARY

In consideration of the above circumstances, the present disclosure provides a hardness deriving device, a medical imaging system, a hardness deriving method, and a storage medium stored with a hardness deriving program, which are capable of consistently measuring the hardness of breast tissue.

A first aspect of the present disclosure is a hardness deriving device including an acquisition section configured to acquire plural ultrasound images obtained by ultrasound imaging a breast in a state in which the breast is pressed by a pressing member at a plurality of different pressures; and a deriving section configured to find an amount of change at corresponding points between the plurality of ultrasound images acquired by the acquisition section, and to derive information indicating a hardness of tissue of the breast based on the amount of change at the corresponding points.

The deriving section of the hardness deriving device in the above aspect may be configured to take pixels at corresponding sites in the breast in each of the plural ultrasound images acquired by the acquisition section as the corresponding points, and to derive the information indicating the hardness of the tissue of the breast based on an amount of change in pixel value of the pixels at the corresponding points.

The deriving section of the hardness deriving device in the above aspect may be configured to take pixels at corresponding sites in the breast in each of the plural ultrasound images acquired by the acquisition section as the corresponding points, and to derive the information indicating the hardness of the tissue of the breast based on an amount of change in position of the pixels at the corresponding points.

The hardness deriving device of the above aspect may further include a display controller configured to control display, on a display section, of an elastographic image obtained by using colors according to the hardness indicated by the information derived by the deriving section.

In the hardness deriving device of the above aspect, the acquisition section may be configured to further acquire a radiographic image imaged by irradiating the breast with radiation in a state in which the breast is pressed by the pressing member, and the display controller may be configured to control display on the display section the radiographic image and the elastographic image, either side-by-side or superimposed on each other.

The hardness deriving device of the above aspect may further include a region of interest reception section configured to receive specification of a region of interest in either the radiographic image or the elastographic image being displayed on the display section, and the display controller may be configured to detect a position of the region of interest received by the region of interest reception section in an image in which the region of interest was specified from the radiographic image or the elastographic image, and to control display of information indicating a position corresponding to the detected position of the region of interest in the image in which the region of interest has not been specified.

The acquisition section of the hardness deriving device in the above aspect may be configured to acquire the plural ultrasound images from an ultrasound imaging device that performs ultrasound imaging of the breast by scanning the breast with ultrasound waves in a state in which the breast is pressed by the pressing member at the plural different pressures, and the hardness deriving device may further include an imaging controller configured to detect a position of an image of an object of interest in the radiographic image, and to control the ultrasound imaging device such that a speed of scanning ultrasound waves is slower at a position corresponding to the detected position of the object of interest image than at another position.

In the hardness deriving device of the above aspect, the acquisition section may be configured to acquire the plural ultrasound images from an ultrasound imaging device that performs ultrasound imaging of the breast by scanning the breast with ultrasound waves in a state in which the breast is pressed by the pressing member at the plural different pressures, the display controller may be configured to display the radiographic image on the display section. The hardness deriving device may further include an object of interest image reception section configured to receive indication of an image of an object of interest in the radiographic image being displayed on the display section, and an imaging controller configured to detect a position of the object of interest image received by the object of interest image reception section from the radiographic image, and to control the ultrasound imaging device such that a speed of scanning ultrasound waves is slower at a position corresponding to the detected position of the object of interest image than at another position.

The acquisition section of the hardness deriving device of the above aspect may be configured to acquire the plural ultrasound images from an ultrasound imaging device that performs ultrasound imaging of the breast by scanning the breast with ultrasound waves in a state in which the breast is pressed by the pressing member at the plural different pressures, and the hardness deriving device of the above aspect may further include an imaging controller configured to control the ultrasound imaging device such that a speed of scanning ultrasound waves is slower at a position of a region of interest corresponding to an object of interest included in the breast that at another position.

The hardness deriving device of the above aspect may further include an alert section configured to display information indicating a position of tissue of the breast that is harder than a threshold value hardness and to issue an alert in cases in which a hardness indicated by the information derived by the deriving section is harder than the threshold value hardness.

The hardness deriving device of the above aspect may further include a hardness reception section configured to receive setting of the threshold value hardness, and the alert section of the hardness deriving device of the above aspect may be configured to display information indicating a position of tissue of the breast that is harder than the threshold value hardness received by the hardness reception section and to issue an alert.

A second aspect of the present disclosure is a medical imaging system including an ultrasound imaging device configured to perform ultrasound imaging of a breast by scanning the breast with ultrasound waves in a state in which the breast is pressed by a pressing member at plural different pressures and to output plural ultrasound images that have been imaged, and the hardness deriving device of the first aspect configured to acquire with the acquisition section the plural ultrasound images that have been output from the ultrasound imaging device.

A third aspect of the present disclosure is a hardness deriving method including acquiring plural ultrasound images obtained by ultrasound imaging a breast in a state in which the breast is pressed by a pressing member at plural different pressures, employing the plural acquired ultrasound images to find an amount of change at corresponding points between the plural ultrasound images, and deriving information indicating a hardness of tissue of the breast based on the amount of change at the corresponding points.

A fourth aspect of the present disclosure is a non-transitory storage medium storing a program that causes a computer to execute hardness deriving processing, the hardness deriving processing including acquiring plural ultrasound images obtained by ultrasound imaging a breast in a state in which the breast is pressed by a pressing member at plural different pressures, employing the plural acquired ultrasound images to find an amount of change at corresponding points between the plural ultrasound images, and deriving information indicating a hardness of tissue of the breast based on the amount of change at the corresponding points.

Thus, the present disclosure may provide a hardness deriving device, a medical imaging system, a hardness deriving method, and a storage medium stored with a hardness deriving program, which are capable of consistently measuring the hardness of breast tissue.

BRIEF DESCRIPTION OF THE DRAWINGS

Exemplary embodiments will be described in detail based on the following figures, wherein:

FIG. 15 is a schematic diagram to explain a method in the second exemplary embodiment for determining a position to change scan speed on the upper face of a press plate from a radiographic image.

DETAILED DESCRIPTION

Detailed explanation follows regarding exemplary embodiments of the present disclosure, with reference to the drawings. Note that the present disclosure is not limited to the following exemplary embodiments.

First Exemplary Embodiment

Figure 1:
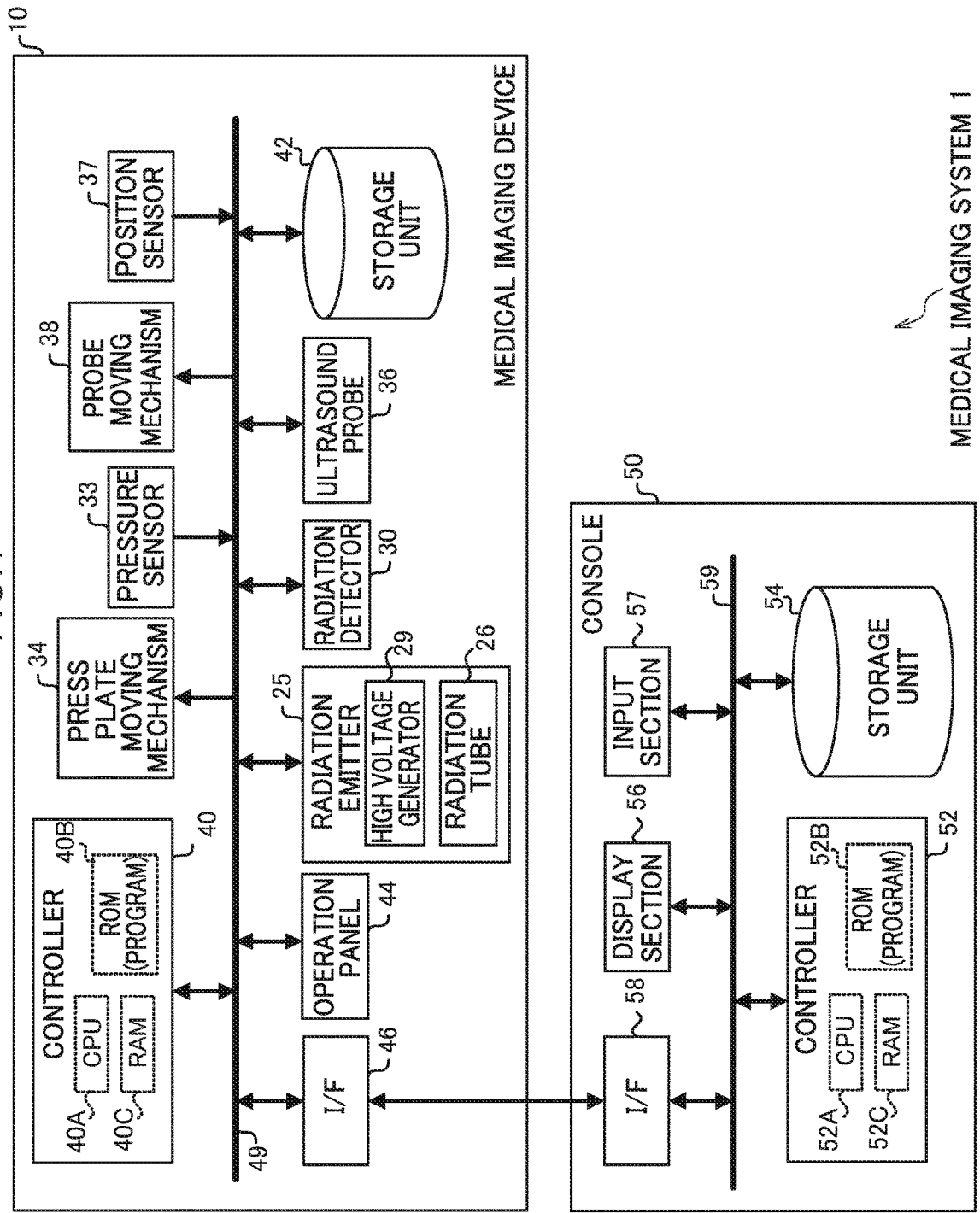
FIG. 1 is a block diagram illustrating a configuration of a medical imaging device and a console in a medical imaging system of a first exemplary embodiment.

As illustrated in FIG. 1, a medical imaging system 1 of the first exemplary embodiment includes a medical imaging device 10 and a console 50.

The medical imaging device 10 combines functionality of a mammography machine that performs radiographic imaging by radiating radiation R onto a breast of a subject and detecting the radiation R that has passed through the breast, and functionality of a ultrasound imaging device that performs ultrasound imaging by transmitting ultrasound waves through the breast, and receiving an ultrasound echo reflected by the interior of the breast.

There are two types of ultrasound imaging performed by the medical imaging device 10 of the present exemplary embodiment: normal ultrasound imaging (described in detail later), and ultrasound imaging for elastography. In the exemplary embodiments, "elastography" refers to detecting the hardness of breast tissue, rather than the overall hardness of the breast, as breast hardness. In the medical imaging system 1 of the present exemplary embodiment, the ultrasound images captured by the medical imaging device 10 are employed to provide a user with images illustrating the results of elastography (referred to below as "elastographic images").

Note that in the exemplary embodiments, "user" refers to a person who performs diagnosis, observation and the like of a site of interest of the breast, and "operator" refers to a person who performs radiographic imaging or ultrasound imaging. The "user" and the "operator" may be the same person, or may be different people.

Figure 2:
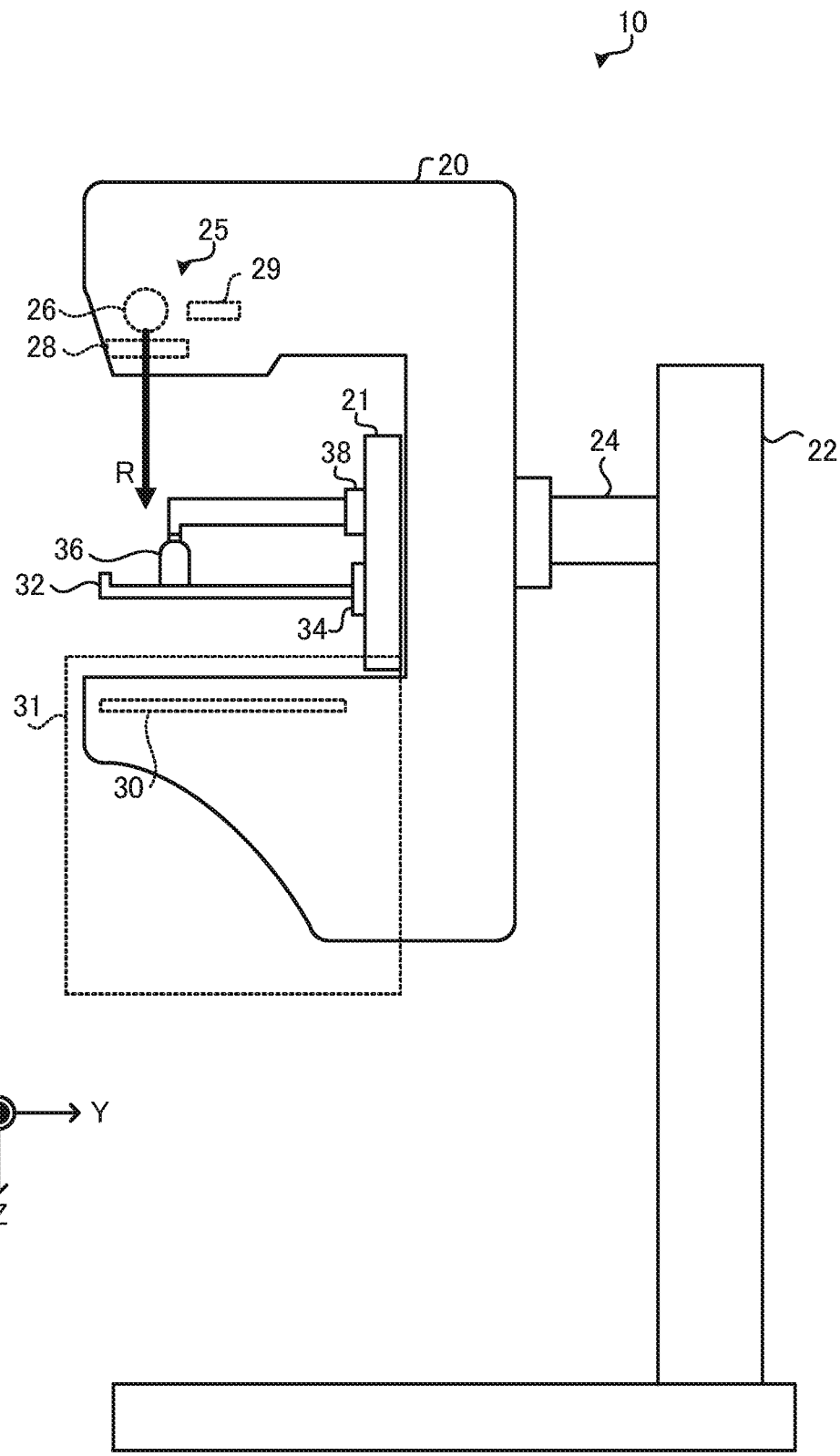
FIG. 2 is a side view illustrating the external appearance of an imaging section of the medical imaging device of the first exemplary embodiment.

Explanation follows regarding configuration of the medical imaging device 10 according to the present exemplary embodiment, with reference to FIG. 2.

As illustrated in FIG. 2, the medical imaging device 10 of the present exemplary embodiment includes an arm 20, a stand 22, and a shaft 24. The stand 22 holds the arm 20 so that the arm 20 is movable in the up-down direction (the Z axis direction). The shaft 24 connects the arm 20 to the stand 22. The arm 20 is able to rotate relative to the stand 22 about a rotation axis of the shaft 24.

A radiation emitter 25, an imaging table 31, and a press unit 21 are provided to the arm 20.

The radiation emitter 25 includes a radiation tube 26, a filter 28, and a high voltage generator 29. The radiation tube 26 generates radiation R by application of a tube voltage. The filter 28 is manufactured from a material such as molybdenum (Mo) or rhodium (Rh), and selectively allows desired wavelength components, among plural wavelength components contained in the radiation R generated by the radiation tube 26, to pass through.

In order to perform imaging, the breast of a subject is positioned on the imaging table 31. From the perspectives of transmissivity to radiation R and strength, the imaging table 31 and the like, with which the breast of the subject makes contact, are formed from a carbon composite, for example. A radiation detector 30 is disposed inside the imaging table 31 for detecting radiation R that has passed through the breast and the imaging table 31. Radiographic images are generated based on the radiation R detected by the radiation detector 30. There are no particular limitations to the type of the radiation detector 30 of the present exemplary embodiment, and, for example, an indirect conversion type of radiation detector may be employed that converts radiation R into light and then converts the converted light into electric charges, or a direct conversion type of radiation detector may be employed that converts the radiation R directly into electric charges.

The press unit 21 is provided with a press plate 32, a press plate moving mechanism 34, an ultrasound probe 36, and a probe moving mechanism 38. The press unit 21 and the arm 20 are configured so as to be separately rotatable relative to the stand 22 about the shaft 24. In the present exemplary embodiment, gears are respectively provided to the shaft 24, the arm 20, and the press unit 21. The arm 20 and the press unit 21 are each coupled to the shaft 24 by switching meshed/unmeshed states between the gears. One or both of the arm 20 and the press unit 21 coupled to the shaft 24 so as to rotate integrally with the shaft 24.

The press plate 32 is moved in the up-down direction (the Z axis direction) by the press plate moving mechanism 34, and presses the breast of the subject against the imaging table 31. The press plate 32 is preferably optically transparent in order to confirm positioning and the pressed state during pressing of the breast, and is formed from a material having excellent transmissivity to the radiation R in order to readily transmit the radiation R emitted from the radiation emitter 25. The press plate 32 is also preferably formed from a material that readily propagates ultrasound waves transmitted from the ultrasound probe 36. Examples of materials that may be employed for the press plate 32 include resins such as polymethylpentene, polycarbonate, acrylic, and polyethylene terephthalate. Polymethylpentene is particularly appropriately employed as the material of the press plate 32 due to having a low rigidity, excellent extensibility and flexibility, and also having appropriate values of sound impedance, which influences the reflectivity of ultrasound waves, and attenuation coefficient, which influences ultrasound wave attenuation.

The ultrasound probe 36 is moved by the probe moving mechanism 38 along the upper face of the press plate 32 (the face on the opposite side to the side where the breast of the subject is disposed), and acquires an ultrasound image of the breast by scanning the breast with ultrasound waves. The ultrasound probe 36 includes plural ultrasound transducers (not illustrated in the drawings) arrayed in one dimension or in two dimensions. Each of the ultrasound transducers transmits ultrasound waves according to a drive signal applied thereto, and outputs a reception signal by receiving an ultrasound echo.

Each of the plural ultrasound transducers is, for example, configured by a vibration element having electrodes formed on both ends of a material having piezoelectric properties (a piezoelectric body), such as a piezoelectric ceramic as typified by Pb (lead) zirconate titanate (PZT), or a polymer piezoelectric element as typified by polyvinylidene difluoride (PVDF). The piezoelectric body expands and contracts when a drive signal of a pulse shape or a continuous wave is transmitted to the electrodes of the vibration element and a voltage is applied thereto. Pulse shaped or continuous wave ultrasound waves are generated from the respective vibration elements by the expansion and contraction, and an ultrasound wave beam is formed by these ultrasound waves combining. The respective vibration elements also expand and contract on receiving propagating ultrasound waves, and generate an electrical signal. These electrical signals are output as ultrasound reception signals, and are input to a controller 40 through a cable (not illustrated in the drawings).

In order to perform ultrasound imaging, the ultrasound probe 36 is moved along the upper face of the press plate 32 in a state in which the upper face of the press plate 32 has been coated in an acoustic matching member such as an echo jelly (described in detail below, see FIG. 5). In the medical imaging device 10 of the present exemplary embodiment, ultrasound imaging is performed automatically, without an operator moving the ultrasound probe 36, by the controller 40 moving the ultrasound probe 36 using the probe moving mechanism 38. Note that there is no limitation to this configuration, and ultrasound imaging may be performed by an operator moving the ultrasound probe 36.

As illustrated in FIG. 1, the medical imaging device 10 of the present exemplary embodiment also includes a pressure sensor 33, a position sensor 37, the controller 40, a storage unit 42, an operation panel 44, and an interface (I/F) 46. The radiation emitter 25, the radiation detector 30, the pressure sensor 33, the press plate moving mechanism 34, the ultrasound probe 36, the position sensor 37, the probe moving mechanism 38, the controller 40, the storage unit 42, the operation panel 44, and the interface (I/F) 46 are connected together by a bus 49, such as a system bus or a control bus, so as to be capable of exchanging various signals with each other.

The controller 40 includes a central processing unit (CPU) 40A, read only memory (ROM) 40B, and random access memory (RAM) 40C. Various programs, etc. to be executed by the CPU 40A are pre-stored in the ROM 40B. The RAM 40C temporarily stores various data.

The pressure sensor 33 detects pressure applied to the press plate 32. The position sensor 37 is internally installed in the ultrasound probe 36, and detects the position of the ultrasound probe 36 (the position on the upper face of the press plate 32).

The controller 40 controls the overall operation of the medical imaging device 10. The controller 40 of the present exemplary embodiment controls the radiation emitter 25, the radiation detector 30, and the press plate moving mechanism 34 so as to perform radiographic imaging. Based on the detection results of the pressure sensor 33, the controller 40 causes the press plate moving mechanism 34 to move the press plate 32 and press the breast against the imaging table 31. The controller 40 adjusts the imaging conditions, such as the tube voltage and the tube current, such that the radiation R is emitted from the radiation emitter 25 by applying a high voltage generated by the high voltage generator 29 to the radiation tube 26. The controller 40 performs radiographic imaging by causing the radiation detector 30 to detect the radiation R that has passed through the breast.

In order to perform ultrasound imaging, the controller 40 of the present exemplary embodiment controls the ultrasound probe 36 and the probe moving mechanism 38 in a state in which the breast is being pressed by the press plate 32. The controller 40 acquires the position of the ultrasound probe 36 based on the detection results of the position sensor 37, and causes the probe moving mechanism 38 to move the ultrasound probe 36. The controller 40 thereby performs ultrasound imaging by transmitting and receiving ultrasound waves, while moving the ultrasound probe 36 with the probe moving mechanism 38. In cases in which the controller 40 of the present exemplary embodiment performs ultrasound imaging for elastography, two ultrasound images are each imaged with the breast pressed by the press plate 32 at different respective pressures.

The respective image data of the radiographic images, ultrasound images, and elastographic images obtained by imaging, and various other data, is stored in the storage unit 42. Specific examples of the storage unit 42 include a hard disk drive (HDD), a solid state drive (SSD) and the like.

The operation panel 44 receives instructions relating to imaging (such as instructions to press the breast with the press plate 32) from an operator. The operation panel 44 is, for example, provided on the arm 20 of the medical imaging device 10. The operation panel 44 may be provided as a touch panel that is a combination of a display section and an input section.

The I/F 46 performs communication of various information, such as with a console 50 and an external system (such as a radiology information system (RIS)), using wireless communication or wired communication. In the medical imaging device 10 of the present exemplary embodiment, the radiographic images and ultrasound images that have been imaged are transmitted from the I/F 46 to the console 50 and to an external device such as a reading device.

As illustrated in FIG. 1, the console 50 of the present exemplary embodiment includes a controller 52, a storage unit 54, a display section 56, an input section 57, and an I/F 58. The controller 52, the storage unit 54, the display section 56, the input section 57, and the I/F 58 are connected together by a bus 59, such as a system bus or a control bus, so as to be capable of exchanging various signals with each other.

The controller 52 includes a CPU 52A, ROM 52B, and RAM 52C. Various programs, etc., including a hardness deriving program, to be executed by the CPU 52A are pre-stored in the ROM 52B. The RAM 52C temporarily stores various data.

The controller 52 controls overall operation of the console 50. The controller 52 of the present exemplary embodiment instructs the medical imaging device 10 to perform radiographic imaging and ultrasound imaging based on an imaging menu.

The controller 52 of the present exemplary embodiment controls the display on the display section 56 of radiographic images and ultrasound images obtained with the medical imaging device 10. Moreover, the controller 52 generates elastographic images from the ultrasound images obtained by the medical imaging device 10, and controls display of the generated elastographic images on the display section 56.

The respective image data of the radiographic images, ultrasound images, and elastographic images obtained by the medical imaging device 10, and various other data, are stored in the storage unit 54. Specific examples of the storage unit 54 include an HDD and an SSD.

The display section 56 displays information related to performing radiographic imaging and ultrasound imaging. The display section 56 also displays radiographic images, ultrasound images, and elastographic images.

The input section 57 receives instructions related to imaging from the operator performing radiographic imaging and ultrasound imaging, and instructions from the operator or the user related to display of the radiographic images, ultrasound images, and elastographic images. Note that the console 50 may be equipped with a touch panel that is a combination of the display section 56 and the input section 57.

The I/F 58 performs communication of various information between the medical imaging device 10 and an external system, such as an RIS, using wireless communication or wired communication.

Next, explanation follows regarding radiographic imaging and ultrasound imaging performed by the medical imaging device 10 of the present exemplary embodiment.

The medical imaging device 10 of the present exemplary embodiment has an imaging mode to perform consecutive radiographic imaging and ultrasound imaging (referred to below as a "consecutive imaging mode"), and an imaging mode to perform either one of radiographic imaging or ultrasound imaging. Explanation follows regarding execution of the consecutive imaging mode by the medical imaging device 10. As mentioned above, the consecutive imaging mode by the medical imaging device 10 of the present exemplary embodiment includes two types of ultrasound imaging: normal ultrasound imaging and ultrasound imaging for elastography.

Figure 3:
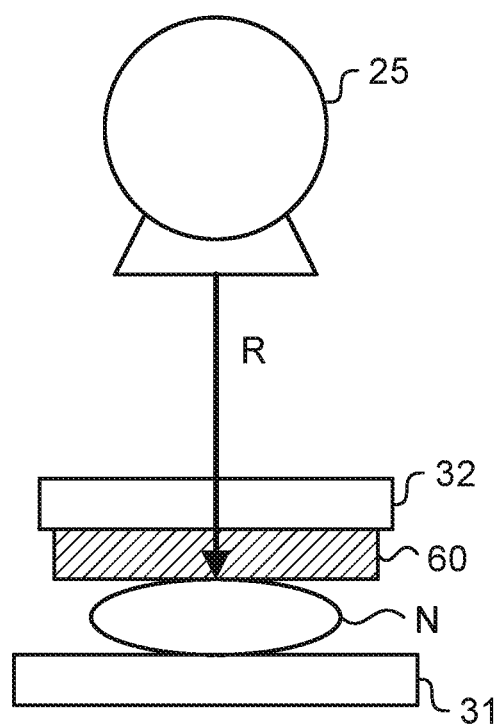
FIG. 3 is an explanatory diagram of a case in which imaging of radiographic images is performed in a consecutive imaging mode in the medical imaging device of the first exemplary embodiment.

In the medical imaging device 10 of the present exemplary embodiment, generally, when performing ultrasound imaging of a breast in a state pressed by the press plate 32, an acoustic matching member is provided between the press plate 32 and the breast in order to reduce non-uniformity in the impedance to ultrasound waves at the contact plane between the press plate 32 and the breast. In cases in which the consecutive imaging mode is executed in the medical imaging device 10, in order to consecutively perform both radiographic imaging and ultrasound imaging while maintaining a state in which the press plate 32 presses the breast continuously until radiographic imaging and ultrasound imaging have been completed, without releasing the pressing of the breast, an acoustic matching member 60, which is not required for radiographic imaging, is provided between the press plate 32 and the breast N even during radiographic imaging, as in the example illustrated in FIG. 3.

The acoustic matching member 60 provided between the press plate 32 and the breast N in the medical imaging device 10 of the present exemplary embodiment is made of a material that exhibits both good compatibility to a biological object (the breast N in the present exemplary embodiment) and transmissivity to ultrasound waves. The acoustic matching member 60 is preferably formed from a material that is physically strong while being soft, that has good transmissivity to ultrasound waves, and that is also capable of withstanding sterilization treatment. Examples of materials that may be employed as the acoustic matching member 60 include non-water containing gel substances such as urethane rubbers and silicone rubbers, and water containing polymer gels such as polyvinyl alcohols and polyethylene oxides. Note that in order to retain shape, a gel pad, in which the surface of the acoustic matching member 60 is covered by a silicone rubber or the like, is employed as the acoustic matching member 60 in the medical imaging device 10 of the present exemplary embodiment.

Note that for an imaging mode in which only radiographic imaging of the breast is performed in the medical imaging device 10 of the present exemplary embodiment, radiographic imaging may be performed without providing the acoustic matching member 60 between the press plate 32 and the breast.

Figure 4:
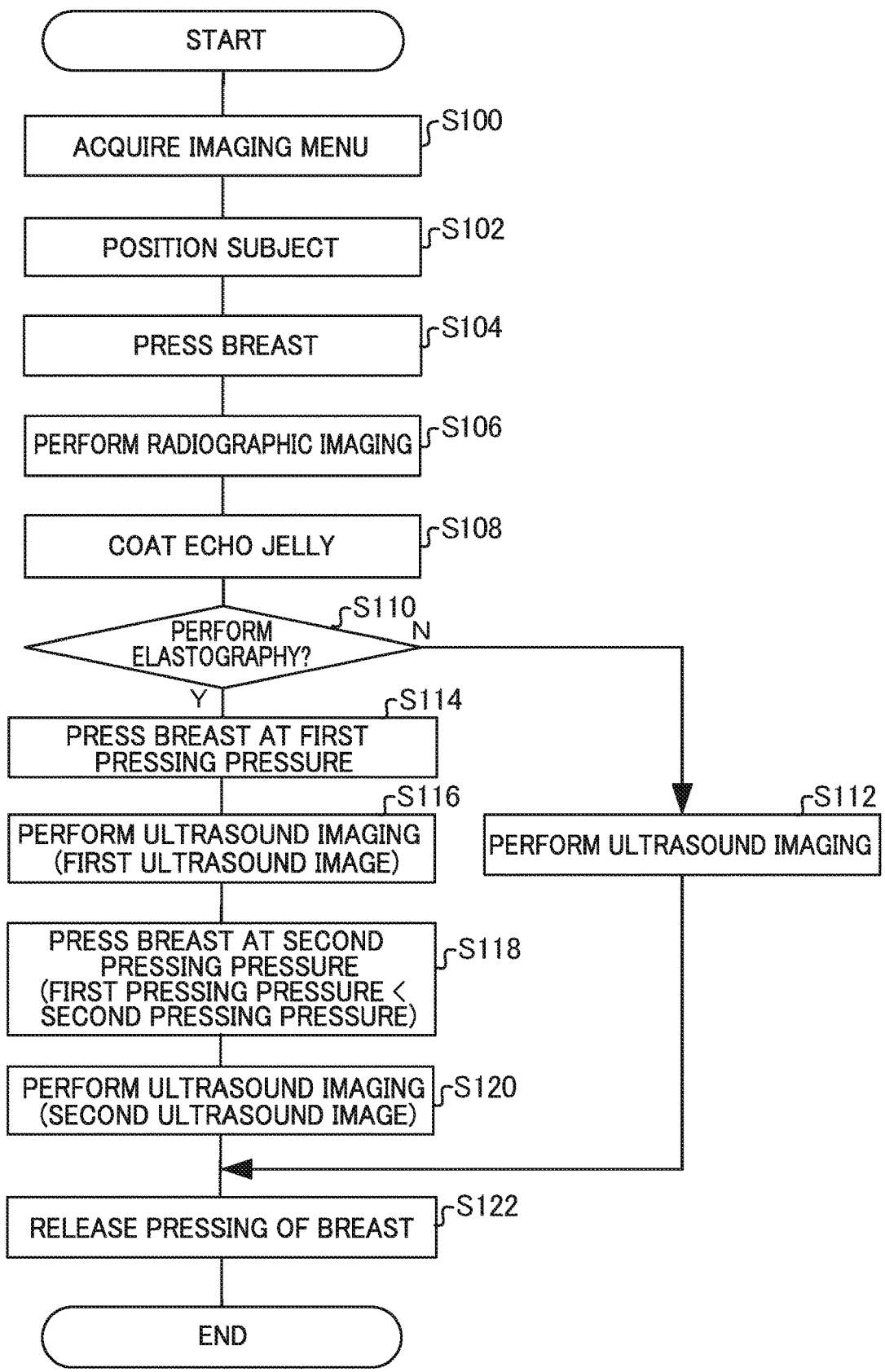
FIG. 4 is a flowchart illustrating an overall flow of imaging operation in a consecutive imaging mode in which radiographic imaging and ultrasound imaging are consecutively performed by the medical imaging device of the first exemplary embodiment.

FIG. 4 illustrates the overall flow of a chain of an imaging operation in cases in which an operator employs the medical imaging device 10 (medical imaging system 1) of the present exemplary embodiment to perform radiographic imaging and ultrasound imaging in the consecutive imaging mode.

First, at step S100, the controller 52 of the console 50 acquires an imaging menu. Information, such as information related to the imaging conditions, the subject, and the breast N, and information relating to whether or not to perform ultrasound imaging for elastography, is included in the imaging menu. For example, the controller 52 may acquire the imaging menu from an external system or the like through the I/F 58, or may acquire the imaging menu input by the operator through the input section 57.

At the next step S102, the operator positions the breast N of the subject on the imaging table 31.

Then, at the next step S104, the controller 40 of the medical imaging device 10 causes the press plate 32 to press the breast N of the subject in a state in which the acoustic matching member 60 is provided on the upper face of the breast N (the face on the side of the press plate 32). Specifically, after the positioning, the operator inputs an instruction through the operation panel 44 to move the press plate 32. The controller 40 causes the press plate moving mechanism 34, according to the instruction input by the operator, to press the breast N in a state sandwiching the acoustic matching member 60 against the breast N, by moving the press plate 32 in the direction to approach the imaging table 31. Note that the pressing of the breast N in the present step in radiographic imaging is performed to spread the breast N out and achieve a uniform thickness of the breast N in order to separate overlapping mammary gland tissue, as well as to reduce the exposure dose, and is performed at a pressing pressure that depends on the subject, the state of the breast N, and the like.

Note that there are no particular limitations to the method of providing the acoustic matching member 60 on the upper face of the breast N when pressing the breast N with the press plate 32. The acoustic matching member 60 may be configured so as to be attachable to the face of the press plate 32 on the breast side, and the breast N may be pressed by the press plate 32 in a state in which the acoustic matching member 60 has been attached to the press plate 32. The breast N may also be pressed by the press plate 32 in a state in which the operator has placed the acoustic matching member 60 on the breast N.

At the next step S106, the medical imaging device 10 performs radiographic imaging of the breast N. During radiographic imaging, the controller 40 causes the probe moving mechanism 38 to retract the ultrasound probe 36 to outside of the radiographic image detection region detected by the radiation detector 30. The image data of the radiographic image that has been imaged is output to the console 50. The image data of the radiographic image may be output to the console 50 immediately after radiographic imaging, or the image data may be first stored in the storage unit 42, and then, after completing the radiographic imaging and ultrasound imaging, both sets of image data may be output to the console 50 together.

Figure 5:
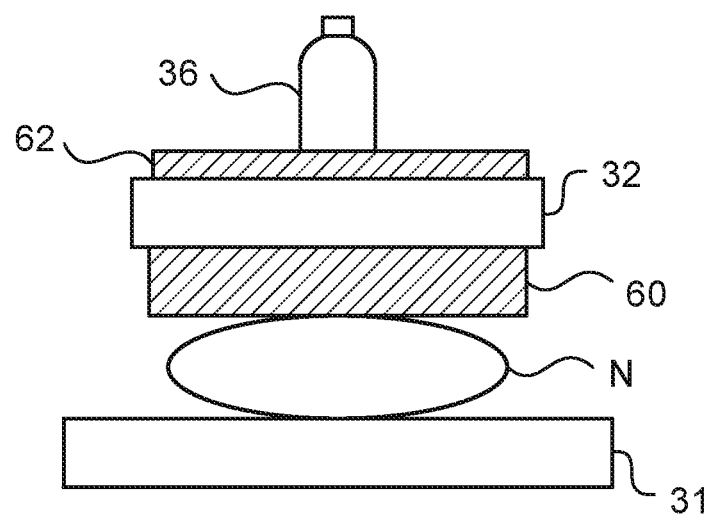
FIG. 5 is an explanatory diagram of a case in which ultrasound imaging is performed in the medical imaging device of the first exemplary embodiment.

After the radiographic imaging, at the next step S108, the operator coats echo jelly 62 onto the upper face of the press plate 32 (the face on the opposite side to the face where the breast N is disposed), as illustrated in the example in FIG. 5. The echo jelly 62 is also an acoustic matching member. As the echo jelly 62, a low viscosity obstetric gel having, for example, components of distilled water, a moisturizer (at least one of propylene or glycol), a macromolecule polymer, soluble lanolin, a colorant, a perfume, and a preservative (at least one of propylparaben or antiseptic methylparaben), having a neutral pH value in the range of from 6.5 to 7.0, and viscosity from 25000 cps to 45000 cps is suitably employed.

At the next step S110, the controller 40 of the medical imaging device 10 determines whether or not to perform ultrasound imaging for elastography. In the medical imaging device 10 of the present exemplary embodiment, determination is made as to whether or not to perform ultrasound imaging for elastography based on information related to whether or not to perform ultrasound imaging for elastography included in the imaging menu acquired at step S100.

After coating of the echo jelly 62 has been completed, the operator inputs an instruction through the operation panel 44 instructing imaging of an ultrasound image. The controller 40 executes the present steps after input of an instruction by the operator has been detected. Negative determination is made in cases in which normal ultrasound imaging is to be performed, and processing proceeds to step S112.

At step S112, the medical imaging device 10 performs normal ultrasound imaging, and then processing proceeds to step S122. In the present exemplary embodiment, "normal ultrasound images" refer to ultrasound images imaged without employing the adjustment used in elastography of the pressure applied to the breast N by the press plate 32. The normal ultrasound images are ultrasound images employed during ordinary diagnosis, observation, etc., and are, for example, ultrasound images in a B (brightness) mode.

As described above, the controller 40 causes the probe moving mechanism 38 to move the ultrasound probe 36 along the face of the press plate 32 coated in the echo jelly 62 (the face facing the radiation tube 26), while detecting the position of the ultrasound probe 36 using the position sensor 37. The controller 40 performs ultrasound imaging by transmitting ultrasound waves from the ultrasound probe 36 at the breast N, and receiving an ultrasound echo reflected by the interior of the breast N.

Affirmative determination is made at step S110 in cases in which imaging for elastography is to be performed, and processing proceeds to step S114.

At step S114, the medical imaging device 10 presses the breast N at a predetermined first pressing pressure. Specifically, the controller 40 causes the press plate moving mechanism 34 to move the press plate 32 in a direction approaching or a direction moving away from the imaging table 31, such that a state is achieved in which the detection result of the pressure sensor 33 is the first pressing pressure.

Then, at the next step S116, the medical imaging device 10 performs ultrasound imaging. The method of ultrasound imaging may be similar to that at step S112, or may differ, for example, by differing from step S112 in the movement speed with which the probe moving mechanism 38 moves the ultrasound probe 36. In the following, an ultrasound image of the breast N imaged in a state pressed at the first pressing pressure is referred to as a "first ultrasound image". Moreover, an ultrasound image of the breast N imaged in a state pressed at a second pressing pressure, described in detail later, is referred to as a "second ultrasound image". First ultrasound images and second ultrasound images are referred to collectively simply as "ultrasound images".

At the next step S118, the medical imaging device 10 presses the breast N at the predetermined second pressing pressure. Specifically, the controller 40 causes the press plate moving mechanism 34 to move the press plate 32 in the direction approaching the imaging table 31, such that a state is achieved in which the detection result of the pressure sensor 33 is the second pressing pressure. Note that in the present exemplary embodiment, the second pressing pressure is a higher pressure than the first pressing pressure (i.e., first pressing pressure<second pressing pressure).

If the first pressing pressure is higher than the second pressing pressure, in contrast to the present exemplary embodiment, constraint on the breast by the press plate 32 and the imaging table 31 is loosened by changing the pressing pressure from the first pressing pressure to the second pressing pressure. In such cases, this might lead to a body movement of the subject due to the constraint loosening. Hence in the medical imaging device 10 of the present exemplary embodiment, the second pressing pressure is set to a higher pressure than the first pressing pressure. In such cases, constraint on the breast by the press plate 32 and the imaging table 31 is tightened by changing the pressing pressure from the first pressing pressure to the second pressing pressure. There is less chance of a body movement of the subject in cases in which the constraint is tightened, than in cases in which the constraint is loosened. If a body movement of the subject were to occur, then a change would arise in the position and shape, etc. of the breast N between the first ultrasound image imaged at step S116, and the second ultrasound image imaged at step S120, described later, resulting in a reduction in the detection precision of the hardness of the tissue of the breast N. Hence, in order to suppress body movement of the subject, the second pressing pressure is a higher pressure than the first pressing pressure in the present exemplary embodiment.

Note that as long as the second pressing pressure is a higher pressure than the first pressing pressure, there are no particular limitations to the specific pressures of the first pressing pressure and the second pressing pressure. For example, one of the first pressing pressure or the second pressing pressure may be the same as the pressing pressure with which the breast N was pressed at step S104. From the perspective of suppressing body movement of the subject as described above, the first pressing pressure is preferably the same as the pressing pressure with which the breast N is pressed at step S104. The controller 40 does not need to perform the processing of step S114 in cases in which the first pressing pressure is the same as the pressing pressure with which the breast N is pressed at step S104.

The specific first pressing pressure and second pressing pressure, or the difference between the second pressing pressure and the first pressing pressure, may be predetermined in the device from the perspectives of body movement of the subject, change to the shape, etc. of the breast N, and deriving the hardness of the tissue of the breast N.

At the next step S120, the medical imaging device 10 images the second ultrasound image similarly to at step S116.

After completing the ultrasound imaging in the above manner, processing proceeds to step S122. The image data of each of the ultrasound images that have been imaged are output to the console 50. The image data of each of the ultrasound images may be output to the console 50 immediately after imaging each of the ultrasound images, or the image data may be first stored in the storage unit 42, and then, after completing the radiographic imaging and ultrasound imaging, the image data of the images arising therefrom may be output to the console 50.

At step S122, the medical imaging device 10 releases pressing of the breast N by the press plate 32. Specifically, the operator inputs an instruction through the operation panel 44 to move the press plate 32 (inputs an instruction to release pressing). The controller 40 causes the press plate moving mechanism 34, according to the instruction input by the operator, to releases pressing of the breast N by moving the press plate 32 in the direction away from the imaging table 31.

After the pressing of the breast N has been released in this manner, the imaging operation of the consecutive imaging mode is ended. The console 50 acquires image data of the radiographic image, and image data of the normal ultrasound image or the first ultrasound image and second ultrasound image, output from the medical imaging device 10, and stores the output images in the storage unit 54.

Figure 6:
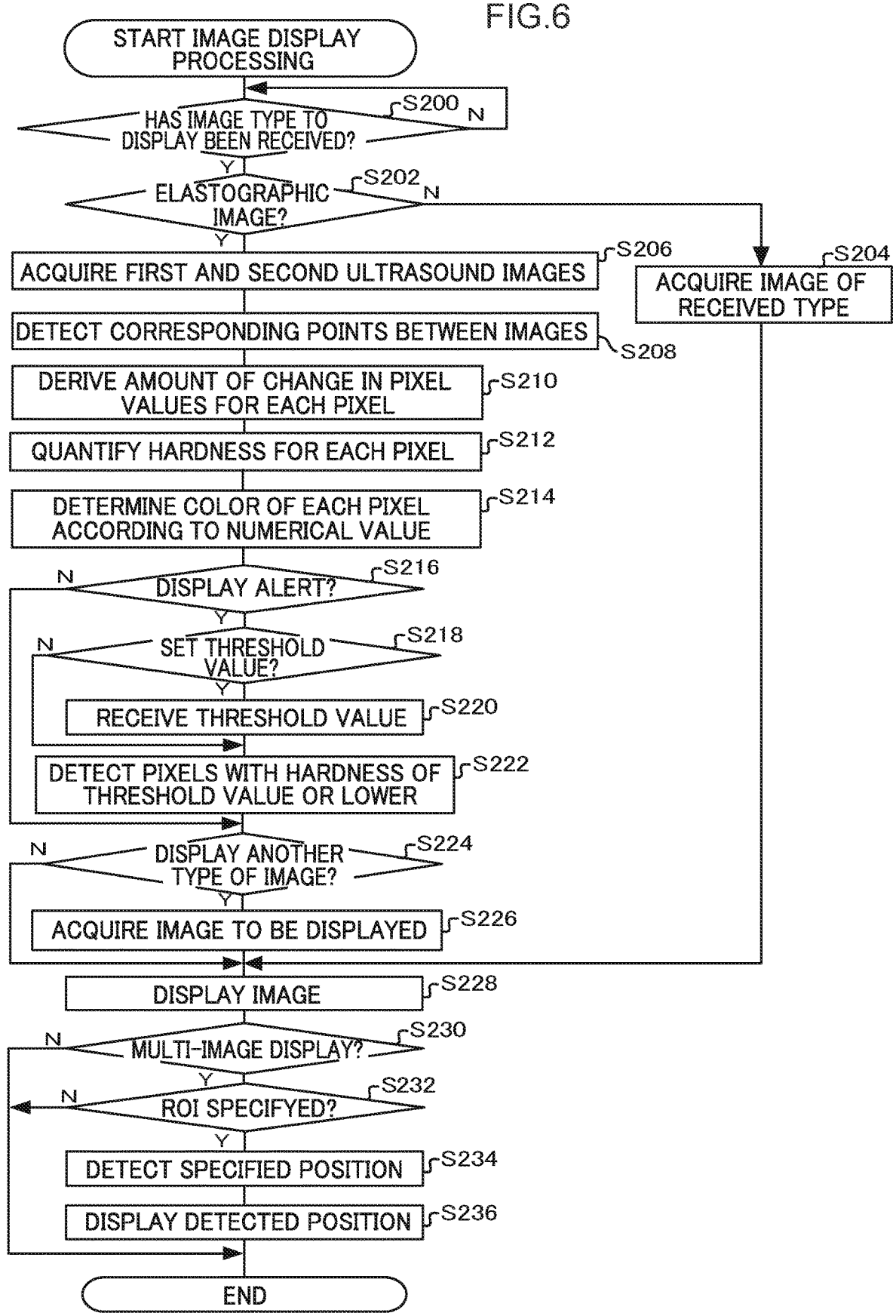
FIG. 6 is a flowchart illustrating a flow of image display processing in the console of the first exemplary embodiment.

In the console 50, image display processing is executed according to instruction from the user to display the radiographic image, the normal ultrasound image, and the elastographic image on the display section 56. In the following, the radiographic image, the normal ultrasound image, and the elastographic image are referred to collectively simply as "images". FIG. 6 is a flowchart illustrating a flow of image display processing executed by the console of the present exemplary embodiment.

The image display processing displayed in FIG. 6 is executed in cases in which an instruction to display an image has been given by the user through the input section 57.

At step S200, the controller 52 determines whether or not an image type to display has been received. Specifically, determination is made as to whether or not an instruction to display an image type has been received from the user through the input section 57. Negative determination is made and a standby state maintained until an image type has been received. Affirmative determination is made when an image type has been received, and processing proceeds to step S202. Regarding images of the same type as those in the storage unit 54, for example, in cases in which there are plural images stored that have been imaged at different times, or plural images stored of different subjects or different breasts N, etc., the user, in addition to the image type, also indicates which image is to be displayed by indicating information to identify the image to be displayed (for example, image identification (ID) information, imaging subject W identification information, or the like) through the input section 57.

At step S202, the controller 52 determines whether or not an elastographic image is included in the received image type. Negative determination is made in cases in which an elastographic image is not included, and processing proceeds to step S204.

At step S204, the controller 52 acquires the image of the received type from the storage unit 54, and then processing proceeds to step S228. In cases in which, as described above, information to identify an image is received, the image corresponding to the received information is acquired.

Affirmative determination is made at step S202 in cases in which an elastographic image is included in the received image type, and processing proceeds to step S206.

At step S206, the controller 52 acquires the first ultrasound image and the second ultrasound image from the storage unit 54. In cases in which, as described above, information to identify the images is received, the first ultrasound image and second ultrasound image corresponding to the received information are acquired.

At the next step S208, the controller 52 detects corresponding points in the first ultrasound image and the second ultrasound image. There are no particular limitations to the method of detecting the corresponding points. For example, during imaging of the first ultrasound image and second ultrasound image, the position of the ultrasound probe 36 in the first ultrasound image and the second ultrasound image may be stored associated with the position of pixels in each of the ultrasound images, and pixels having the same associated ultrasound probe 36 position may be detected as corresponding points in each of the first ultrasound image and the second ultrasound image.

At the next step S210, the controller 52 derives an amount of change in the pixel value of each of the pixels. In the present exemplary embodiment, as an example, the controller 52 derives an amount of change in pixel value for each of the pixels by subtracting the pixel value of the pixel in the first ultrasound image from the pixel value of the pixel in the second ultrasound image at each corresponding point (second ultrasound image pixel value—first ultrasound image pixel value).

At the next step S212, the controller 52 quantifies the hardness of the breast N tissue for each of the pixels. Although there are no particular limitations to the method of quantifying the hardness, the controller 52 of the present exemplary embodiment quantifies the hardness by employing a predetermined constant, the amount of change in pixel value for each of the pixels derived at step S210, and the difference between the second pressing pressure and the first pressing pressure, and quantifying by applying the definition of Equation (1) below to each of the pixels.

$$\text{Hardness} = \text{constant} \times (\text{shift amount}/(\text{second pressing pressure} - \text{first pressing pressure})) \quad (1)$$

In Equation (1), the constant is a constant obtained experimentally, and may be predetermined in the device. The amount of change is smaller the harder the breast N tissue, and is larger the softer the breast N tissue. Thus, with respect to the numerical value indicating the hardness derived using Equation (1), the smaller the value the harder the breast N, and the larger the value the softer the breast N.

At the next step S214, the controller 52 decides on a color for each of the pixels so as to indicate the hardness of breast N tissue according to the numerical values obtained at step S212. In the console 50 of the present exemplary embodiment, an elastographic image employing colors according to the hardness of breast N tissue similar to those of an elastographic image obtained by ordinary elastography are displayed on the display section 56. In ordinary elastography, an image is displayed that is blue for harder and red for softer. Generally, the breast N tissue is displayed with a red color due to being softer the greater the proportion of fat. The breast N tissue is displayed with red or yellow in cases in which there are benign tumors or mammary glands that are soft, or slightly hard, and with blue as a tumor becomes more malignant (i.e., as the breast cancer having progressed further) due to the tendency to increase in hardness.

Thus, in the console 50 of the present exemplary embodiment, correspondence relationships are predetermined between numerical values and color, such that red color is associated with larger numerical values obtained at step S212, and blue color is associated with smaller numerical values obtained at step S212, and then the controller 52 decides on the color of each of the pixels based on the correspondence relationships between numerical value and color.

At the next step S216, the controller 52 determines whether or not to display an alert. As described above, the harder the tissue, the higher the possibility of a malignant tumor. Thus, configuration may be made such that in cases in which it is determined in the console 50 of the present exemplary embodiment that a numerical value indicating the hardness of the tissue of the breast N is harder than a predetermined hardness, specifically in cases in which the hardness quantified at step S212 is smaller than a predetermined threshold value at each pixel, an alert is displayed due to there being a high possibility of a malignant tumor. Note that configuration may be made such that an alert may be displayed in cases in which the aggregate number of pixels present having a quantified hardness smaller than the predetermined threshold value is a specific number or greater, or exceeds a specific number, and such that an alert is not displayed in cases in which the aggregate number such pixels present is less than the specific number, or is the specific number or less.

In the console 50 of the present exemplary embodiment, whether or not to display such alert may, for example, be preset prior to executing the present image display processing. Moreover, for example, configuration may be made such that the controller 52 is instructed by a user through the input section 57 to display, or not to display, an alert, by displaying a question as to whether or not to display an alert on the display section 56.

Negative determination is made in cases in which an alert is not to be displayed, and processing proceeds to step S224. However, affirmative determination is made in cases in which an alert is to be displayed, and processing proceeds to step S218.

At step S218, the controller 52 determines whether or not to set a threshold value for display of an alert as described above. In the console 50 of the present exemplary embodiment, a predetermined threshold value for display of an alert may be set by a user. The user may accordingly determine whether or not to set the predetermined threshold value. Specifically, the controller 52 may be instructed by the user through the input section 57 regarding whether or not to set the threshold value by displaying on the display section 56 a question as to whether or not to set a threshold value.

Negative determination is made in cases in which a threshold value is not to be set, and processing proceeds to step S222. In cases in which a threshold value is not to be set, a predetermined threshold value in the device is employed for displaying an alert.

However, affirmative determination is made in cases in which a threshold value is to be set, and processing proceeds to step S220. At step S220, the controller 52 receives the setting of the threshold value by the user through the input section 57.

At the next step S222, the controller 52 detects pixels in which the numerical value obtained at step S212 and indicating the hardness of the tissue of the breast N is smaller than the threshold value (less than the threshold value). Note that there is no limitation to the present exemplary embodiment, and the controller 52 may detect pixels having numerical values of hardness of the threshold value or lower.

At the next step S224, the controller 52 determines whether or not to display another type of image other than an elastographic image. Negative determination is made in cases in which the type of image received at step S200 has been only elastographic image, and processing proceeds to step S228. However, affirmative determination is made in cases in which an image other than an elastographic image is included in the types of image received, such as cases in which display of a radiographic image and an elastographic image imaged in the consecutive imaging mode described above is received, and processing proceeds to step S226.

At step S226, the controller 52 acquires an image corresponding to the received image type from the storage unit 54. As described above, in cases in which information to identify the image has been received, the image corresponding to the received information is acquired.

Figure 7:
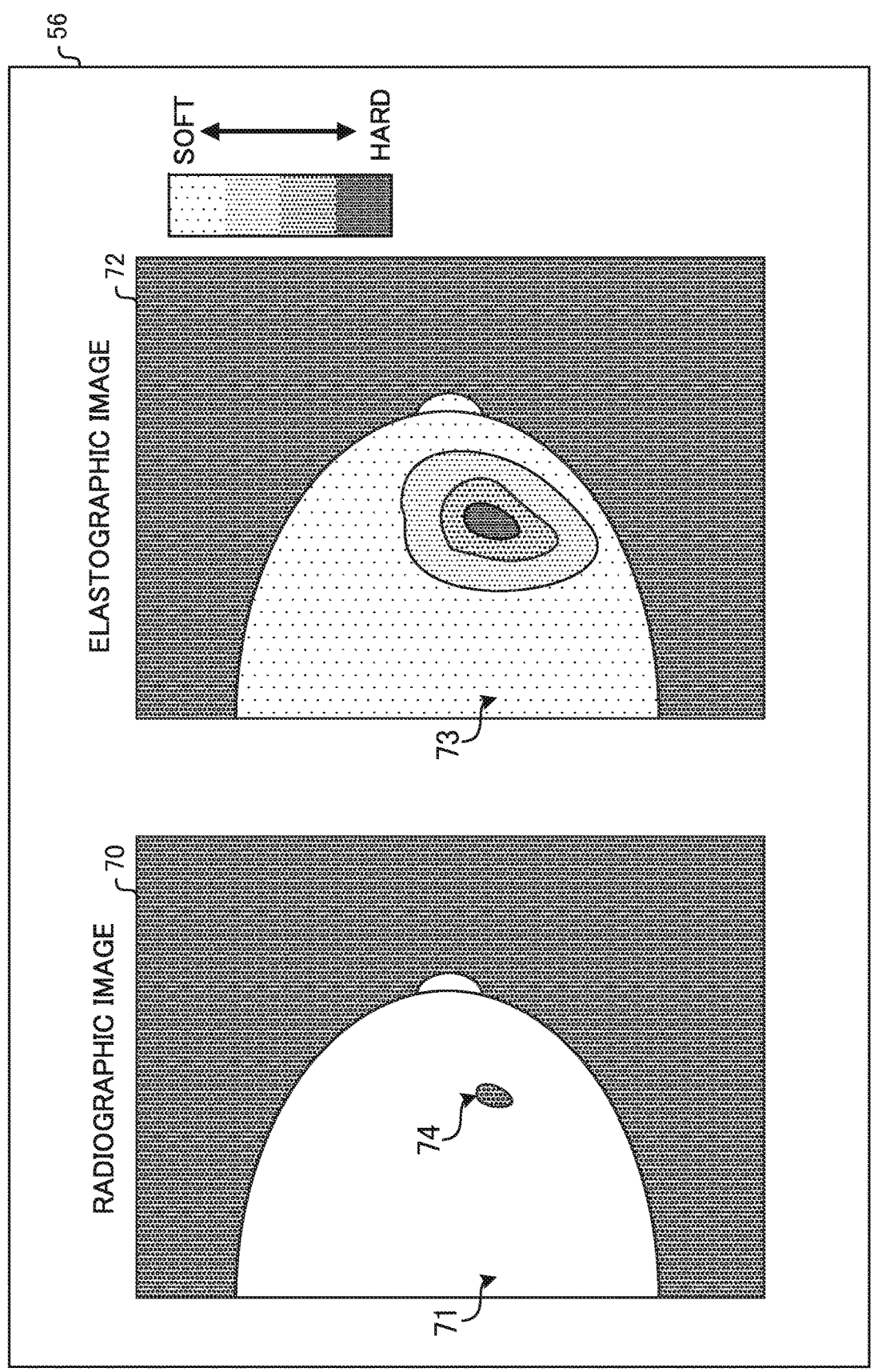
FIG. 7 is a schematic diagram illustrating an example of display in the first exemplary embodiment in a case in which a radiographic image and an elastographic image are displayed side-by-side without displaying an alert.
Figure 8:
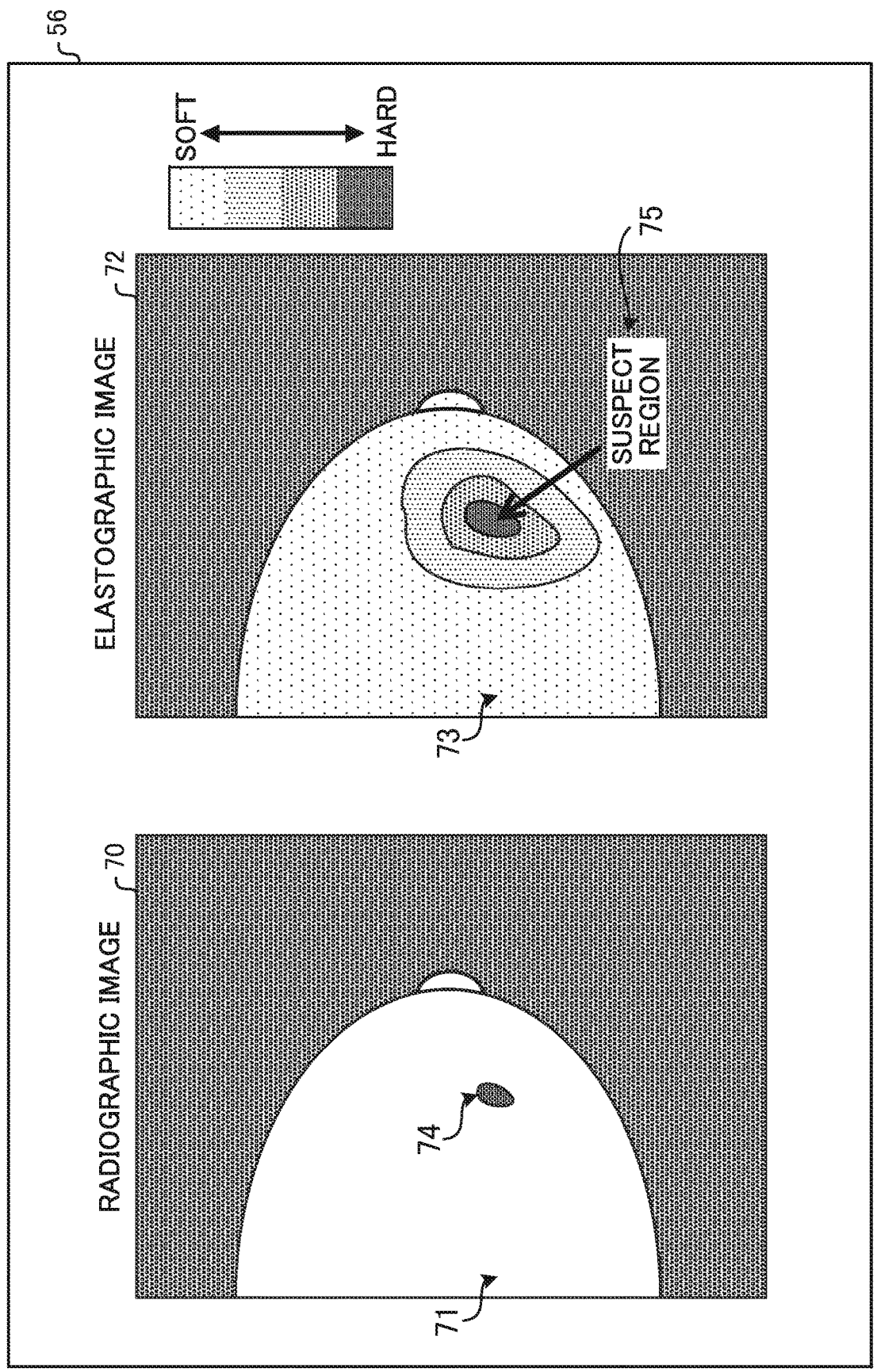
FIG. 8 is a schematic diagram illustrating an example of display in the first exemplary embodiment in a case in which a radiographic image and an elastographic image are displayed side-by-side while displaying an alert.

At the next step S228, the controller 52 displays the image on the display section 56. In the present exemplary embodiment, in cases in which both an elastographic image and a radiographic image are to be displayed, as illustrated in FIG. 7 and FIG. 8, the controller 52 displays a radiographic image 70 and an elastographic image 72 side-by-side on the display section 56. Note that FIG. 7 illustrates an example of a display of the radiographic image 70 and the elastographic image 72 in cases in which an alert is not displayed, and FIG. 8 illustrates an example of a display of the radiographic image 70 and the elastographic image 72 in cases in which an alert is displayed.

In the examples illustrated in FIG. 7 and FIG. 8, a breast image 71 is included in the radiographic image 70, and an object of interest image 74 of an object of interest such as a tumor is included in the breast image 71. Moreover, in the elastographic image 72, for ease of illustration, in addition to employing a color according to hardness, the hardness of the tissue of a breast region 73 is indicated by the density (shade) of dots. It is apparent, from a comparison of the radiographic image 70 and the elastographic image 72, that the tissue of the breast is hard at the position in the elastographic image 72 corresponding to the object of interest image 74 in the radiographic image 70.

Moreover, in the example illustrated in FIG. 8, the controller 52 displays an alert notice 75 when the numerical value of hardness in the elastographic image 72 is less than the threshold value (the region of pixels having dots displayed with the hardest state in the specific example illustrated in FIG. 8). In the example illustrated in FIG. 8, as the alert notice 75, a user's the attention is drawn by indicating, with an arrow, a region of pixels where an alert should be displayed, and displaying "Suspect region". However, the alert notice 75 is not limited thereto.

Note that the display state of the radiographic image 70 and the elastographic image 72 is not limited to display in a side-by-side state as illustrated in the examples of FIG. 7 and FIG. 8. For example, as illustrated in the example in FIG. 9, the radiographic image 70 and the elastographic image 72 may be displayed in a superimposed state. In cases in which the radiographic image 70 and the elastographic image 72 are displayed superimposed on each other, it is preferable for corresponding portions of the breast image 71 and the breast region 73 are superimposed. Therefore, for example, the skin line of the breast may be detected in both images, and the radiographic image 70 and the elastographic image 72 may be displayed such that the detected skin lines are superimposed on each other.

Figure 9:
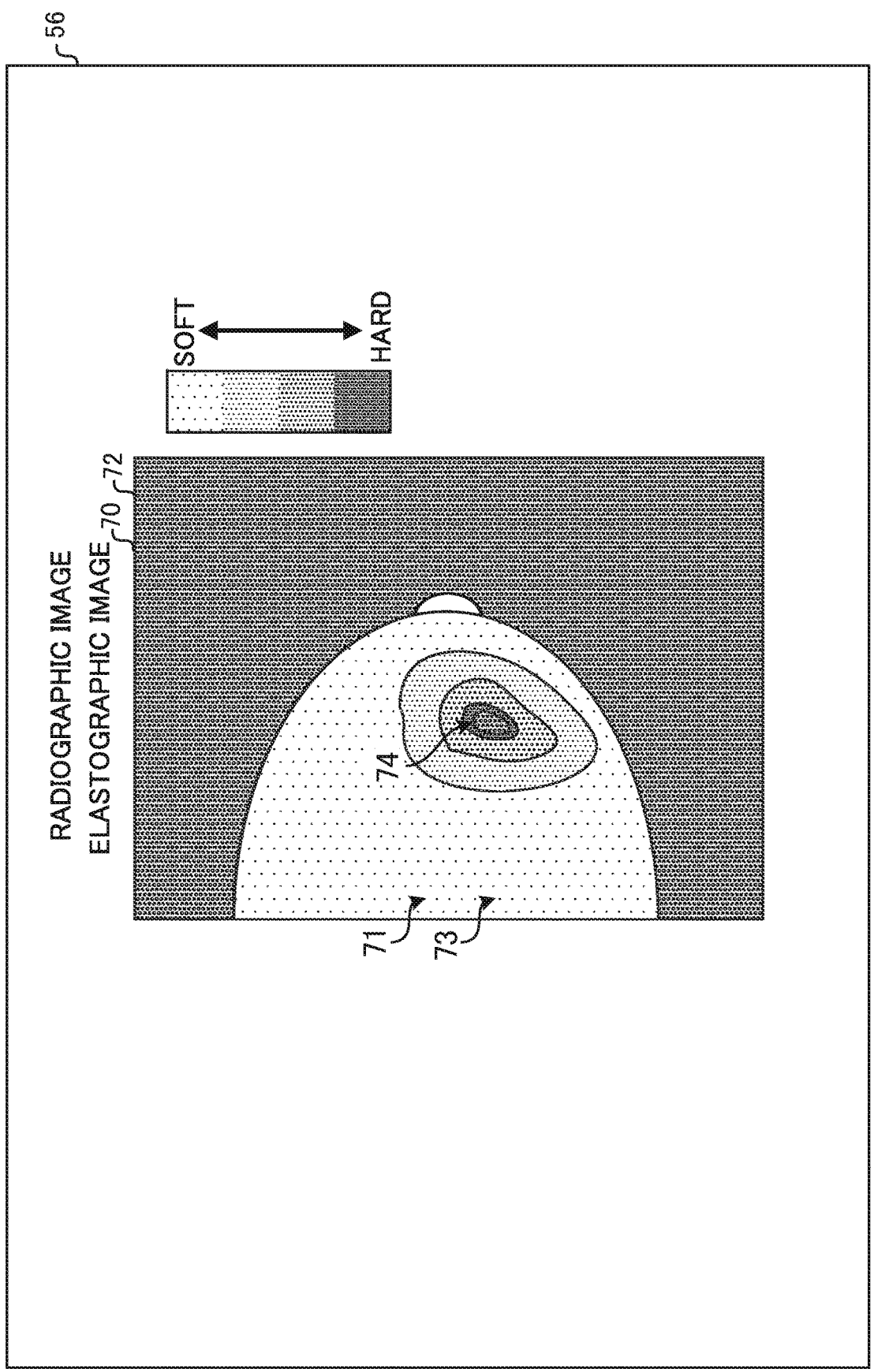
FIG. 9 is a schematic diagram illustrating an example of display in the first exemplary embodiment in a case in which a radiographic image and an elastographic image are displayed superimposed on each other.

Moreover, configuration may be made so as to switch, under instruction from the user or the like, between a side-by-side display state of the radiographic image 70 and the elastographic image 72, as illustrated in the examples of FIG. 7 and FIG. 8, and a superimposed display state thereof, as illustrated in the example of FIG. 9.

In cases in which, for example, an ultrasound image, such as a B mode image, and the elastographic image 72 are displayed on the display section 56, the controller 52 may display the ultrasound image instead of the radiographic image 70 illustrated in FIG. 7 and FIG. 8. In cases in which an ultrasound image and an elastographic image are displayed, a B mode image of either the first ultrasound image or the second ultrasound image may be displayed on the display section 56 as the ultrasound image together with the elastographic image 72. In such cases, execution of the processing of step S226 may be omitted.

After an image including the elastographic image 72 is displayed on the display section 56 as described above, the controller 52 determines at step S230 whether or not to display plural images on the display section 56. Negative determination is made in cases in which plural images are not to be displayed on the display section 56, and the present image display processing is ended. However, affirmative determination is made in cases in which plural images are to be displayed on the display section 56, and processing proceeds to step S232.

At step S232, the controller 52 determines whether or not a user has, through the input section 57, specified on the image being displayed an image indicating a region of interest (ROI). In the console 50 of the present exemplary embodiment, in cases in which plural images are being displayed on the display section 56, an image of a region of interest specified by the user may be corresponded against one of the images, and displayed at a corresponding position in the other image being displayed.

Note that there is no particular limitation to the method of specifying the image indicating an object of interest using the input section 57. For example, a pointing device such as a mouse may be employed as the input section 57, and the image indicating an object of interest may be specified by specifying, in an image being displayed on the display section 56, an image of an object of interest (an object of interest such as abnormal shadowing), a region of interest including the object of interest, or a position of interest (x, y coordinates) of the object of interest, using the input section 57 such as a pointing device. For example, in cases in which the object of interest image 74 of the breast image 71 in the radiographic image 70 is specified, as illustrated in the example in FIG. 10, a user may specify a region of interest 80 including the object of interest image 74 on the display section 56 using the mouse pointer 81 as the pointing device.

Negative determination is made in cases in which specification of an image indicating a region of interest has not been received even though a predetermined duration has elapsed, and the present image display processing is ended. However, affirmative determination is made in cases in which specification of an image indicating a region of interest has been received, and processing proceeds to step S234.

At step S234, the controller 52 detects the position of the specified image indicating the region of interest. The controller 52 first detects the position of the image indicating the region of interest in the specified image. The controller 52 then detects, in the other image, the position corresponding to the detected position. For example, in the example illustrated in FIG. 7, in cases in which the user has specified through the input section 57 the object of interest image 74 in the radiographic image 70, the controller 52 detects the position corresponding to the object of interest image 74 in the elastographic image 72.

Figure 11:
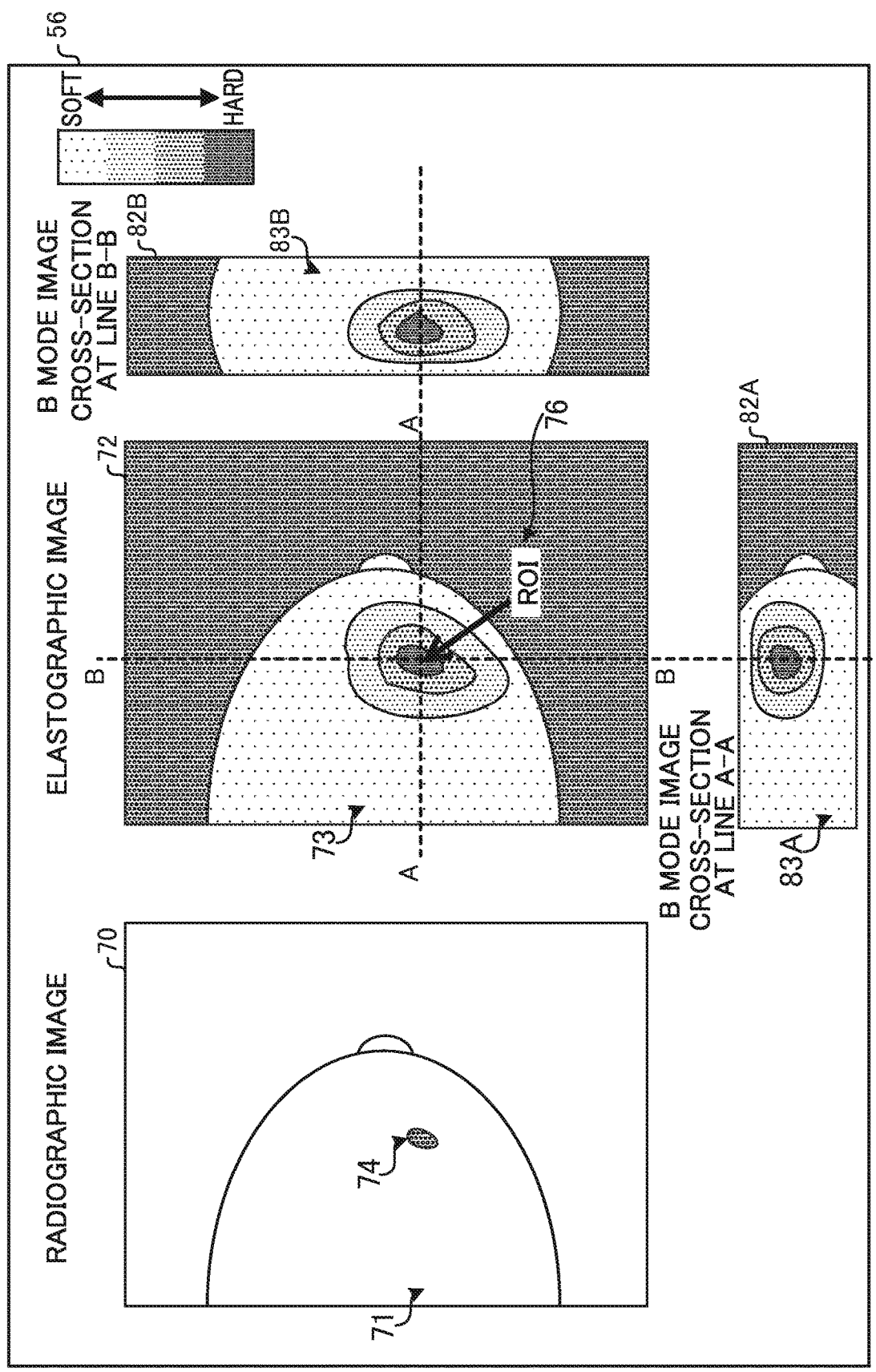
FIG. 11 is a schematic diagram illustrating an example of displaying, in the example illustrated in FIG. 7, a position in an elastographic image corresponding to an object of interest image specified by a user.

At the next step S236, the controller 52 ends the present image display processing after the detected position has been displayed on the display section 56. The example illustrated in FIG. 11 illustrates a case in which information 76 is displayed to indicate the position corresponding to the object of interest image 74. In the example illustrated in FIG. 11, as the information 76, the position corresponding to the object of interest image 74 is indicated to the user by using an arrow to indicate the position corresponding to the object of interest image 74 and displaying "ROI"; however, the information 76 is not limited thereto.

In the present exemplary embodiment, as illustrated in FIG. 11, the controller 52 displays B mode images 82A, 82B corresponding to the detected position, and the elastographic image 72, on the display section 56. In the example illustrated in FIG. 11, the controller 52 first, specifically, finds a center position (or a centroid position) of the object of interest image 74 using image analysis. Then, the controller 52 displays the B mode image 82A of a cross-section at line A-A through the center position (a cross-section in the Y axis direction illustrated in FIG. 2), and the B mode image 82B of a cross-section at line B-B through the center position (a cross-section in the X axis direction illustrated in FIG. 2), in a state that facilitates comparison with the elastographic image 72. For ease of illustration, in FIG. 11, in order to make the position of each of breast regions 83A, 83B clear in the B mode images 82A, 82B corresponding to the position of the breast region 73 in the elastographic image 72, dots of different density (shade) similar to those of the elastographic image 72 are applied to the B mode images 82A, 82B.

Figure 12:
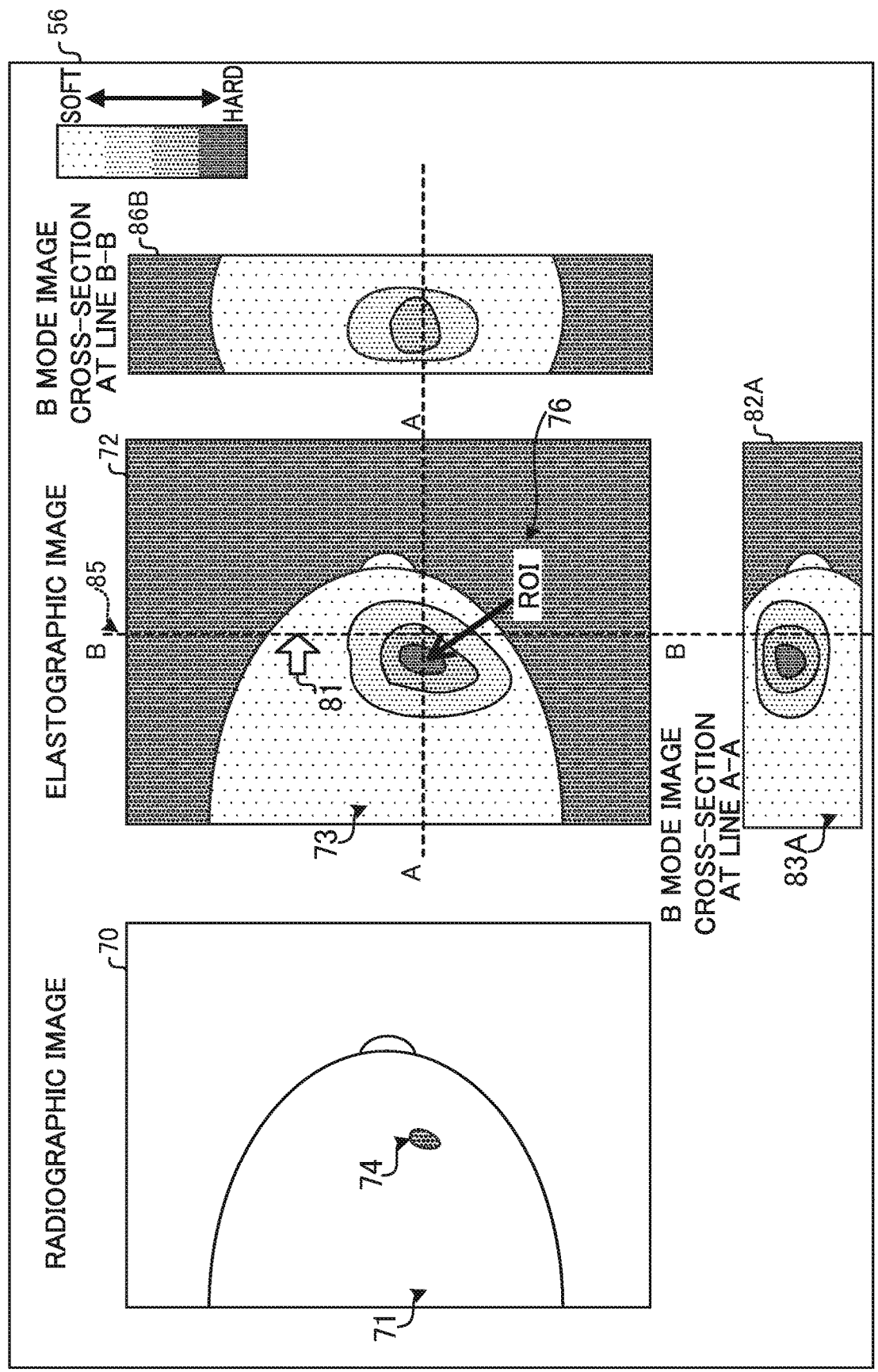
FIG. 12 is a schematic diagram illustrating an example of displaying, in the example illustrated in FIG. 11, a B mode image at a different position.

In cases in which the user has indicated a position on the breast N in a state in which the elastographic image 72 and the B mode images 82A, 82B are displayed on the display section 56, as in the example illustrated in FIG. 11, the controller 52 may change the display on the display section 56 to displaying the B mode images 82A, 82B at cross-sections of the indicated position. FIG. 12 illustrates a specific example in which the user has used the mouse pointer 81 to move the position of display 85 indicating line B-B from a position of the ROI to a position nearer to the nipple. In such cases, instead of the B mode image 82B at the cross-section at line B-B as illustrated in FIG. 11, a B mode image 86B at the cross-section at line B-B for the position indicated by the user is displayed on the display section 56, as illustrated in FIG. 12.

Figure 10:
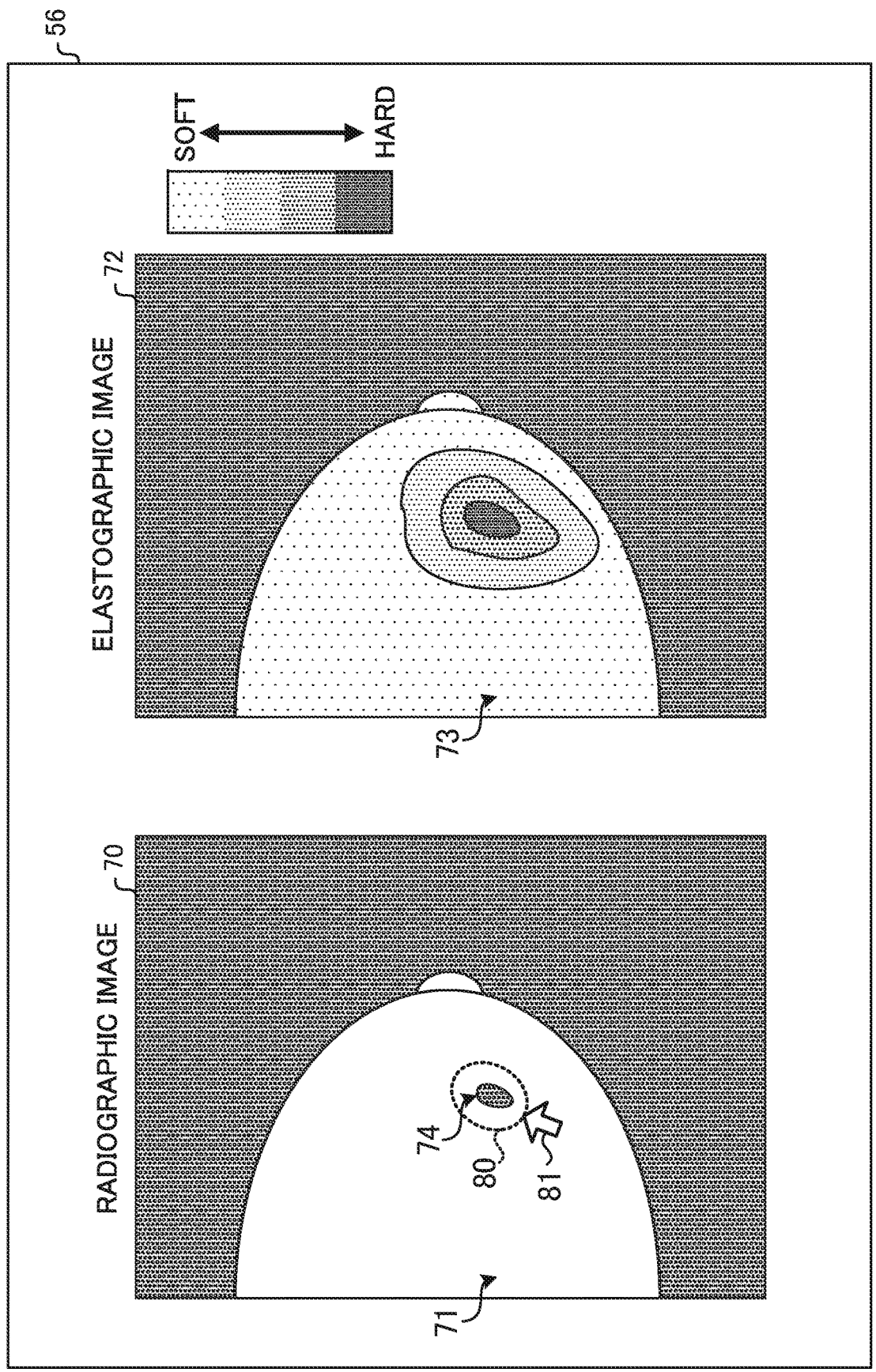
FIG. 10 is a schematic diagram illustrating an example of a state in which a region of interest including an object of interest image has been specified using a mouse pointer, as an example of specifying an object of interest image in a radiographic image in the first exemplary embodiment.

Note that although in the present exemplary embodiment detailed explanation has been given of cases in which, as illustrated in FIG. 10, at step S232 of the image display processing (see FIG. 6), the ROI (the object of interest image 74) is specified on the radiographic image 70, there is no limitation thereto. Obviously, the user may specify the ROI on another image being displayed on the display section 56. For example, the ROI may be specified on the elastographic image 72 in the example illustrated in FIG. 10. In such cases, as described above, the B mode images 82A, 82B corresponding to the position of the ROI specified on the elastographic image 72 are preferably displayed, as illustrated in FIG. 11.

There is no particular limitation to the method of specifying the image indicating the object of interest using the input section 57. For example, a pointing device such as a mouse may be employed as the input section 57, and the image indicating the object of interest may be specified by specifying, in the image being displayed on the display section 56, the image of an object of interest (an object of interest such as abnormal shadowing), a region of interest including the object of interest, or a position of interest (x, y coordinates) of the object of interest, using the input section 57 such as the pointing device. For example, in cases in which the object of interest image 74 of the breast image 71 is specified in the radiographic image 70, a user may employ the mouse pointer 81 as the pointing device to specify the region of interest 80 including the object of interest image 74 on the display section 56, as in the example illustrated in FIG. 10.

Second Exemplary Embodiment

Explanation follows regarding a second exemplary embodiment. Components similar to those of the medical imaging system 1 according to the first exemplary embodiment are appended with the same reference numerals, and detailed explanation thereof is omitted.

Configuration of a medical imaging system 1 is similar to that of the medical imaging system 1 of the first exemplary embodiment (see FIGS. 1 and 2), so explanation thereof is omitted.

In the present exemplary embodiment, the method of imaging the first ultrasound image and the second ultrasound image differs from that of the first exemplary embodiment. In the medical imaging device 10 of the first exemplary embodiment, the first ultrasound image and the second ultrasound image are imaged by scanning the ultrasound probe 36 across the surface of the press plate 32 at a constant (constant within a margin of error) speed using the probe moving mechanism 38. In contrast thereto, in the medical imaging device 10 of the present exemplary embodiment, the first ultrasound image and the second ultrasound image are imaged by slowing the scanning of the ultrasound probe 36 at positions corresponding to the region of interest in the breast N, compared to other positions.

Figure 13:
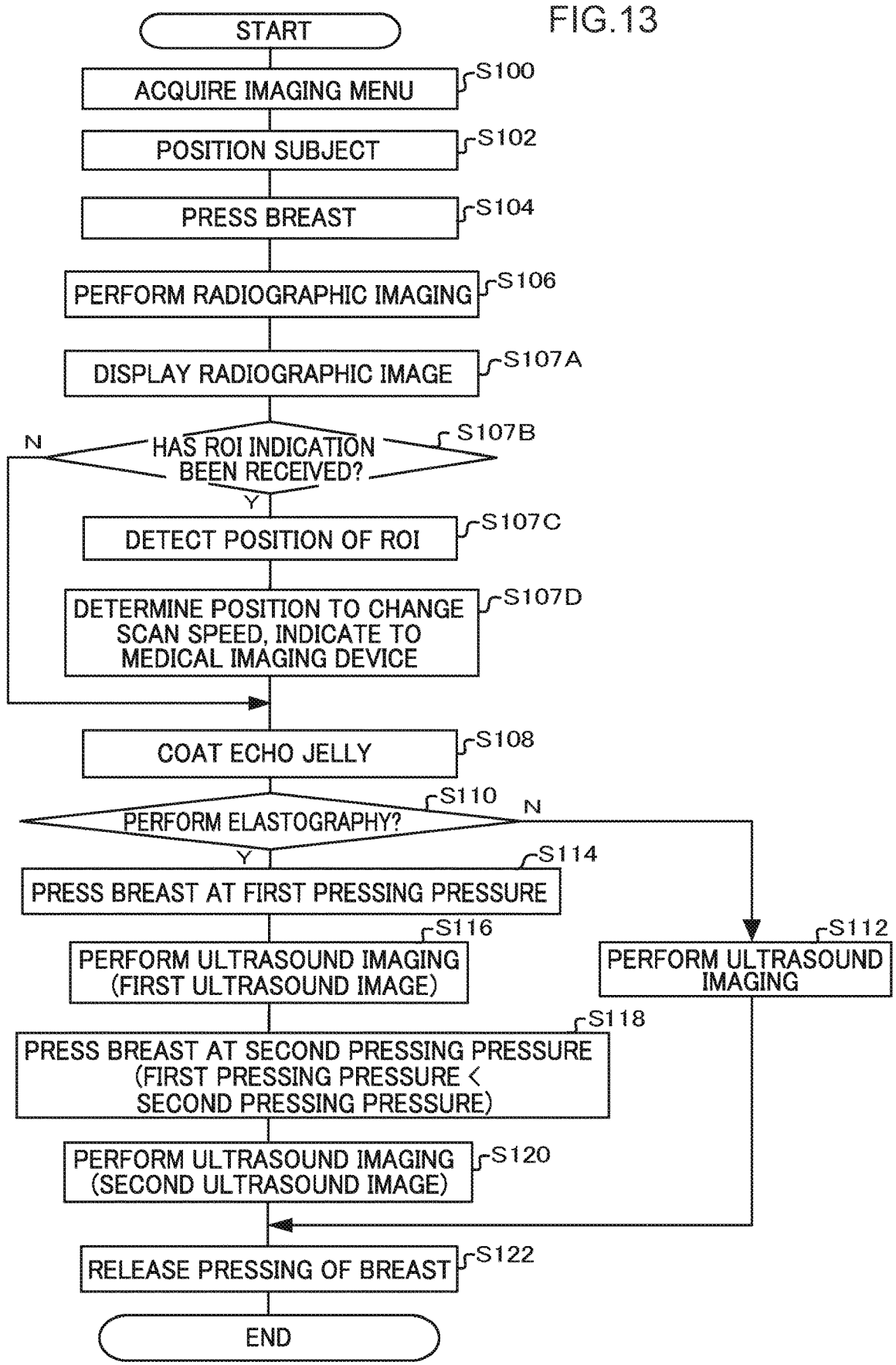
FIG. 13 is a flowchart illustrating an overall flow of imaging operation in a consecutive imaging mode in which radiographic imaging and ultrasound imaging are consecutively performed by a medical imaging device of a second exemplary embodiment.

Hence, as illustrated in FIG. 13, the overall flow of a series of the imaging operation when imaging in the consecutive imaging mode in the medical imaging device 10 of the present exemplary embodiment differs from the flow of the imaging operation when imaging in the consecutive imaging mode in the medical imaging device 10 of the first exemplary embodiment (see FIG. 4), in that the processing of steps S107A to S107D is executed between step S106 and step S108.

In the present exemplary embodiment, image data of a radiographic image imaged by the medical imaging device 10 at step S106 is output to the console 50.

Figure 14:
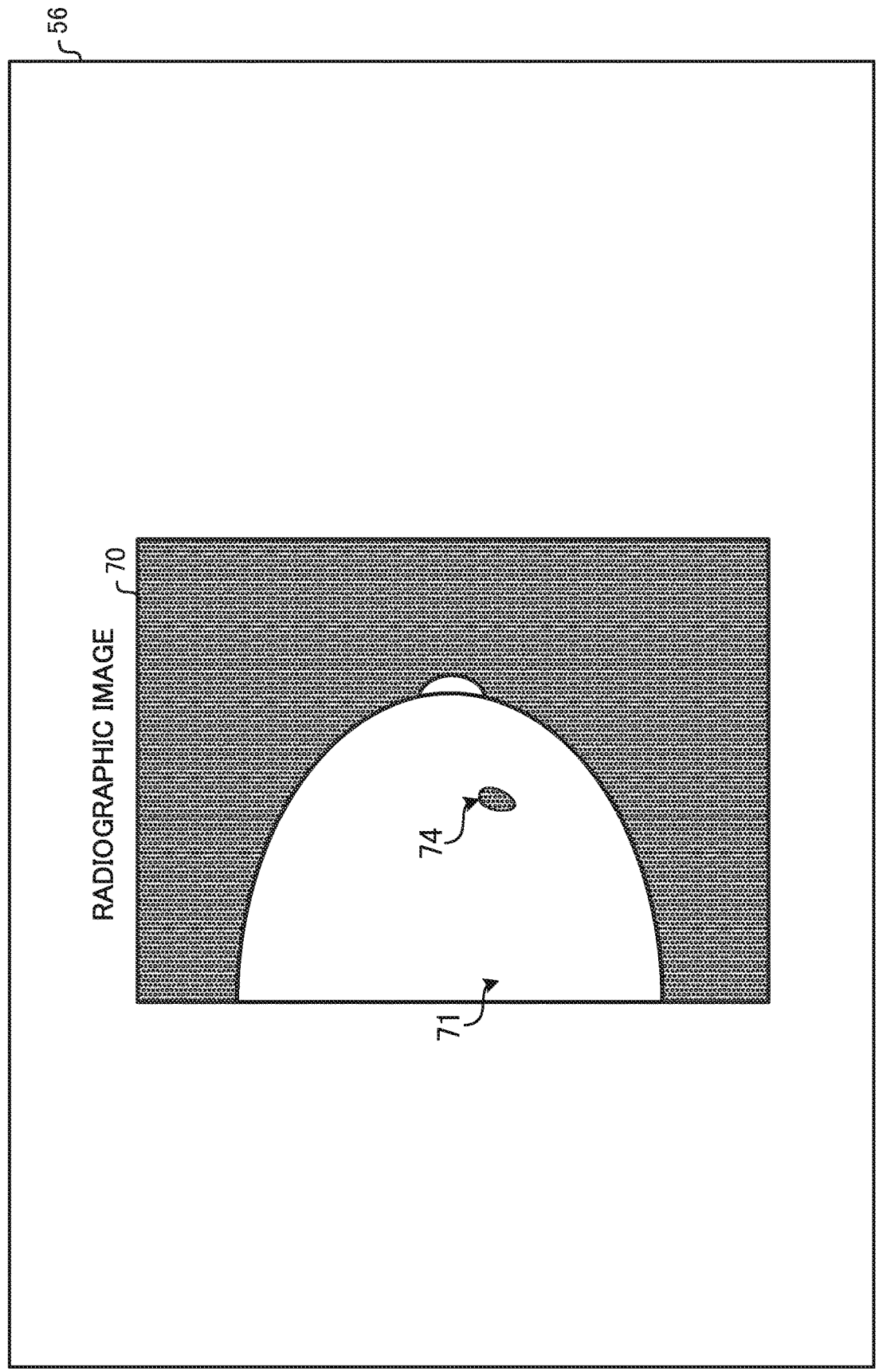
FIG. 14 is a schematic diagram illustrating an example of displaying a radiographic image that a controller of a console has acquired from medical imaging device in the second exemplary embodiment.

At the next step S107A, as illustrated in FIG. 13, the controller 52 of the console 50 displays a radiographic image acquired from the medical imaging device 10 on the display section 56, as illustrated in the example of FIG. 14.

At the next step S107B, the controller 52 determines whether or not an indication has been received from a user through the input section 57 of an image indicating a region of interest (ROI) on the radiographic image 70 being displayed on the display section 56. There is no particular limitation to the method of indicating the image indicating an object of interest using the input section 57 and, for example, the method may be similar to that at step S232 of the image display processing described above in the first exemplary embodiment (see FIG. 6).

Negative determination is made in cases in which specification of an image indicating a region of interest has not be received even though a predetermined duration has elapsed, and processing proceeds to step S108. However, affirmative determination is made in cases in which indication of an image indicating a region of interest has been received, and processing proceeds to step S107C.

At step S107C, the controller 52 detects the position of the indicated image indicating a region of interest in the radiographic image 70. For example, in the example illustrated in FIG. 14, in cases in which the user has indicated the object of interest image 74 through the input section 57, the object of interest image 74 is detected in the radiographic image 70.

In the next step S107D, the controller 52 determines a position (a position on the press plate 32) to change (to slow) the scan speed of scanning of the ultrasound probe 36 during ultrasound imaging, and indicates the determined position to the medical imaging device 10.

The position to change the scan speed is, for example, determined by pre-acquiring correspondence relationships between positions on the surface of the press plate 32 and pixels in the radiographic image 70, and, based on the correspondence relationships, determining a position on the surface of the press plate 32 corresponding to the position of pixels in the image indicating the region of interest detected at step S107C.

In the console 50 of the present exemplary embodiment, as stated above, in cases in which a user has indicated the object of interest image 74 through the input section 57 in the example illustrated in FIG. 14, the position to change the scan speed is determined as a position corresponding to inside a rectangular shaped region 84 on the surface of the press plate 32, as illustrated in the example of FIG. 15, and the position on the press plate 32 is indicated to the medical imaging device 10.

Due to being indicated at step S107D, during imaging of the first ultrasound image at step S116 and during imaging of the second ultrasound image at step S118, which are executed after the present step, the medical imaging device 10 slows the scan speed for scanning the ultrasound probe 36 at positions corresponding to within the rectangular shaped region 84 on the surface of the press plate 32 to slower than at other positions. There are no particular limitations to the degree by which the scan speed is slowed. By slowing the scan speed, the precision by which the hardness of the tissue of the breast N is detected is raised, however, the time the breast is being pressed is also lengthened, and since this increases the burden on the subject, the degree by which the scan speed is slowed may accordingly be predetermined from these perspectives.

Thus, in the medical imaging system 1 of the present exemplary embodiment, by determining that the position where the scan speed is to be changed is the position on the surface of the press plate 32 corresponding to the inside of the rectangular shaped region 84 including the object of interest image 74, the scan speed when scanning the ultrasound probe 36 at the position corresponding to the region of interest extracted from the radiographic image 70 may be made slower than the scan speed at other positions. The medical imaging system 1 of the present exemplary embodiment accordingly enables the precision of detecting the hardness of the object of interest to be raised. Moreover, since the controlling to slow the scan speed is not performed at positions other than in the region of interest, the time during which the breast is pressed may be prevented from becoming longer due to lengthening the time needed to image ultrasound images, and hence the burden on the subject may be reduced.

In the medical imaging system 1 of each of the exemplary embodiments as described above, the controller 52 of the console 50 acquires from the medical imaging device 10 plural ultrasound images (the first ultrasound image and the second ultrasound image) that have been ultrasound imaged with the breast N in states pressed by the press plate 32 at plural different pressures, i.e. at the first pressing pressure and the second pressing pressure. Moreover, the controller 52 of the console 50 employs the acquired first ultrasound image and second ultrasound image to find the amount of change at corresponding points between the first ultrasound image and the second ultrasound image, and derives information indicating the hardness of the tissue of the breast N based on the amount of change (the amount of change in pixel values) at the corresponding points.

Moreover, in the console 50 of each of the above exemplary embodiments, the hardness of the tissue of the breast N is quantified based on the amount of change of the pixel values between respective corresponding sites in the acquired first ultrasound image and the second ultrasound image, and on the difference between the second pressing pressure and the first pressing pressure.

Hitherto, although generally in elastography peripheral tissue is employed for comparison to detect hardness or softness, in the console 50 of the present exemplary embodiment, due to being able to obtain normalized numerical values for the hardness of the tissue of the breast N, the hardness of the tissue of the breast N may be measured consistently as absolute numerical values. The console 50 of the present exemplary embodiment enables consistent measurement of the hardness of the tissue of the breast N, irrespective of such factors as the technical skill of an operator. Appropriate information indicating the hardness of the tissue of the breast N (for example, the elastographic image 72 as described above) may accordingly be derived even in cases in which the operator is inexperienced.

Note that in each of the above exemplary embodiments, although during elastography the breast N is pressed at two pressing pressures, these being the first pressing pressure and the second pressing pressure, ultrasound imaging may be performed by pressing the breast N at each pressing pressure for three or more pressing pressures. For example, the breast N may be pressed at three pressing pressures of a first pressing pressure to a third pressing pressure and imaged in a first ultrasound image to a third ultrasound image. In such cases, for example, an average value (including an average value obtained after weighting) may be taken of a numerical value indicating the hardness of the tissue of the breast N derived from the first ultrasound image and the second ultrasound image, and a numerical value indicating the hardness of the tissue of the breast N derived from the second ultrasound image and the third ultrasound image, so as to derive a final hardness of the tissue of the breast N.

Moreover, in each of the above exemplary embodiments, after imaging the first ultrasound image with the breast N in a state pressed at the first pressing pressure for the whole of the breast N, the second ultrasound image is imaged with the breast N in a state pressed at the second pressing pressure for the whole of the breast N; however, the method of imaging the ultrasound images under each of the pressing pressures is not limited thereto. For example, another method may be employed in which ultrasound waves is transmitted from the ultrasound probe 36 in a state in which the breast N is pressed at the first pressing pressure and an ultrasound echo reflected from inside the breast N received. The breast N is then pressed at the second pressing pressure without moving the ultrasound probe 36, and, after again transmitting ultrasound waves from the ultrasound probe 36 and receiving the ultrasound echo reflected inside the breast N, the ultrasound probe 36 is moved. At the position moved to, after again transmitting ultrasound waves using the ultrasound probe 36 and receiving an ultrasound echo in a state in which the breast N is pressed at the first pressing pressure, ultrasound waves are transmitted by the ultrasound probe 36 and an ultrasound echo is received in a state in which the breast N is pressed at the second pressing pressure. The first ultrasound image and the second ultrasound image for the whole of the breast N may then be imaged by performing repeated cycles of such processing of pressing, transmitting ultrasound waves, receiving ultrasound echoes, and moving the ultrasound probe 36.

Moreover, explanation has been given in each of the above exemplary embodiments of cases in which the medical imaging device 10 includes functionality for radiographic imaging and functionality for ultrasound imaging; however, there is no limitation thereto, and it is sufficient as long as the medical imaging device 10 includes at least functionality for ultrasound imaging. In normal mammography machines, the breast of a subject is in a state pressed by a press plate during radiographic imaging of the breast. However, when performing ultrasound imaging of a breast using a normal ultrasound imaging device, imaging is performed by an operator moving an ultrasound probe over the surface of the breast of a subject. Thus, it may be difficult to observe the site of interest when comparing both images due to differences in the pressed state of the breast of the subject, the imaging state and the like between when performing radiographic imaging and when performing ultrasound imaging. In contrast, by including both functionality for radiographic imaging and functionality for ultrasound imaging as in the medical imaging device 10 of the present exemplary embodiment, the pressed state of the breast of the subject and the imaging conditions may not differ between radiographic imaging and ultrasound imaging. The medical imaging device 10 of the present exemplary embodiment accordingly enables a user to easily compare radiographic images and ultrasound images.

Moreover, the medical imaging device 10 may be a device capable of performing what is referred to as tomosynthesis imaging in which different radiation angles are employed for radiation R radiated onto the breast N, and radiographic imaging is performed at each of the radiation angles. In such cases, the radiographic images obtained in tomosynthesis imaging, and tomographic images obtained by reconstructing the plural radiographic images obtained in tomosynthesis imaging, may be substituted for the radiographic images in each of the above exemplary embodiments, and, for example, displayed on the display section 56 together with the elastographic image.

Moreover, in each of the above exemplary embodiments, an alert is displayed in cases in which the tissue of the breast N is hard based on a predetermined threshold value; however, plural threshold values may be provided, and levels of alert displayed according to the hardness of the tissue of the breast N. Moreover, for example, an alert may be displayed by employing a criterion other than a threshold value. For example, a generally employed diagnostic method may be employed in which color pattern diagnosis is performed on an elastographic image. Color pattern diagnosis is a diagnostic method in which portions in an elastographic image corresponding to tissue inside and at the periphery of a tumor are classified with a score 1 to score 5 according to the color tone (balance between green and blue), with a higher confidence of being malignant the higher the sore. In cases in which color pattern diagnosis is applied, the score at which to display an alert may be preset in the device, or may be set by the user.

Moreover, although in each of the above exemplary embodiments the controller 52 derives information indicating the hardness of the tissue of the breast N based on the amount of change in pixel value of the pixels as an example of an amount of change of pixels at corresponding sites in the breast N in each of the first ultrasound image and the second ultrasound image, there is no limitation thereto. For example, the controller 52 may employ an amount of change in the position of pixels at corresponding sites as an example of the amount of change of pixels. The amount of positional shift, which is the amount by which the position of identified pixels or pixels at feature points in the first ultrasound image (which may each be regions of a single pixel or plural pixels) are shifted in the second ultrasound image, is smaller the harder the tissue of the breast N. Thus, the hardness of the breast may be derived by employing the amount of positional shift, namely the amount of change in position. There are no particular limitations to the method by which corresponding pixels are detected in the first ultrasound image and the second ultrasound image, and, for example, detection may be performed by computer aided diagnosis (CAD). In such cases, the "amount of change" for deriving the hardness in Equation (1) may be taken as the amount of change in position of corresponding pixels.

Moreover, although in each of the above exemplary embodiments, the region of interest was specified by the user or indicated, a region of interest (an image indicating a region of interest) may be automatically detected in an image. For example, a region of interest may be automatically detected in an image using CAD.

Although in the example above the position to change the speed of scanning by the ultrasound probe 36 is determined according to the object of interest image indicated in the radiographic image, there is no limitation being specified in the radiographic image. For example, the first ultrasound image may be displayed on the display section 56, and the position to change the speed of scanning by the ultrasound probe 36 when imaging the second ultrasound image may be determined according to the object of interest image indicated in the first ultrasound image. In such cases, processing corresponding to step S107A to step S107D, in the overall flow of an imaging operation cycle for imaging performed in the consecutive imaging mode illustrated in FIG. 13, may be executed between step S116 and step S117, with the image to be displayed changed to the first ultrasound image.

Moreover, in each of the above exemplary embodiments, although explanation has been given of cases in which the controller 52 of the console 50 has the functionality of all the sections of the hardness deriving device of the present disclosure, there is no limitation to these, and, for example, the functionality of part or all of the sections of the hardness deriving device may be provided in another device, such as the medical imaging device 10.

There are no particular limitations to the radiation R in the above exemplary embodiments, and X-rays, gamma rays, etc. may be employed therefor.

The configuration, operation, and the like of the medical imaging device 10 explained in the above exemplary embodiments are merely examples thereof, and various modifications are possible according to the circumstances within a range not departing from the spirit of the disclosure.

What is claimed is:

1. A hardness deriving device comprising:
   a memory; and
   a processor coupled to the memory, the processor being configured to:
   acquire a first ultrasound image from an ultrasound imaging device that performs ultrasound imaging of a breast by scanning the breast with ultrasound in a state in which the breast is pressed by a pressing plate at a first pressure and by scanning an upper face of the pressing plate with an ultrasound probe, and a second ultrasound image by moving the pressing plate, scanning the breast with ultrasound in a state in which the breast is pressed by the pressing plate at a second pressure that is different from the first pressure, and scanning the upper face of the pressing plate with the ultrasound probe; and
   find an amount of change between a corresponding point of the first ultrasound image and a corresponding point of the second ultrasound image, and to derive information indicating a hardness of tissue of the breast based on the amount of change at the corresponding points and based on the first and second pressures.

2. The hardness deriving device of claim 1, wherein the processor is configured to take pixels at corresponding sites in the breast in each of the first and second ultrasound images as the corresponding points, and to derive the information indicating the hardness of the tissue of the breast based on an amount of change in pixel value of the pixels at the corresponding points.

3. The hardness deriving device of claim 1, wherein the processor is configured to take pixels at corresponding sites in the breast in each of the first and second ultrasound images as the corresponding points, and to derive the information indicating the hardness of the tissue of the breast based on an amount of change in position of the pixels at the corresponding points.

4. The hardness deriving device of claim 3, wherein the processor is configured to:
   acquire the first and second ultrasound images from the ultrasound imaging device that performs ultrasound imaging of the breast by scanning the breast with ultrasound waves in a state in which the breast is pressed by the pressing member at the first and second pressures; and
   control the ultrasound imaging device such that a speed of scanning ultrasound waves is slower at a position of a region of interest corresponding to an object of interest included in the breast than at another position.

5. The hardness deriving device of claim 1, wherein the processor is:
   configured to control display, on a display section, of an elastographic image obtained by using colors according to the hardness indicated by the derived information.

6. The hardness deriving device of claim 5, wherein the processor is configured to:
   further acquire a radiographic image imaged by irradiating the breast with radiation in a state in which the breast is pressed by the pressing member; and
   control display on the display section of the radiographic image and the elastographic image, either side-by-side or superimposed on each other.

7. The hardness deriving device of claim 6, wherein the processor is configured to:
   receive, via an input section, specification of a region of interest in either the radiographic image or the elastographic image being displayed on the display section, and
   detect a position of the region of interest received by the input section in an image in which the region of interest was specified from the radiographic image or the elastographic image, and control display of information indicating a position, corresponding to the position of the region of interest in the image, in which the region of interest has not been specified.

8. The hardness deriving device of claim 6, wherein the processor is configured to:
   detect a position of an image of an object of interest in the radiographic image, and control the ultrasound imaging device such that a speed of scanning ultrasound waves is slower at a position corresponding to the position of the image of the object of interest than at another position.

9. The hardness deriving device of claim 6, wherein the processor is configured to:
   acquire the first and second ultrasound images from the ultrasound imaging device that performs ultrasound imaging of the breast by scanning the breast with ultrasound waves in a state in which the breast is pressed by the pressing member at the first and second pressures;

display the radiographic image on the display section;
receive, via an input section, indication of an image of an object of interest in the radiographic image being displayed on the display section; and
detect a position of the image of the object of interest received by the input section from the radiographic image, and control the ultrasound imaging device such that a speed of scanning ultrasound waves is slower at a position corresponding to the position of the image of the object of interest than at another position.

10. The hardness deriving device of claim 1, wherein the processor is configured to:
display information indicating a position of tissue of the breast that is harder than a threshold value hardness and issue an alert.

11. The hardness deriving device of claim 10, wherein the processor is configured to:
receive, via an input section, setting of the threshold value hardness, and
display information indicating a position of tissue of the breast that is harder than the threshold value hardness received by the input section and issue an alert.

12. A medical imaging system comprising:
an ultrasound imaging device configured to perform ultrasound imaging of a breast by scanning the breast with ultrasound waves in a state in which the breast is pressed by a pressing member at a plurality of different pressures and to output a plurality of ultrasound images that have been imaged; and
the hardness deriving device of claim 1 configured to acquire with the acquisition section the plurality of ultrasound images that have been output from the ultrasound imaging device.

13. The hardness deriving device of claim 1, wherein the processor is configured to acquire the first and second pressures applied to the breast by the pressing plate, from a pressure sensor.

14. A hardness deriving method comprising:
acquiring a first ultrasound images from an ultrasound imaging device that performs ultrasound imaging of a breast by scanning the breast with ultrasound in a state in which the breast is pressed by a pressing plate at a first pressure and by scanning an upper face of the pressing plate with an ultrasound probe, and a second ultrasound image by moving the pressing plate, scanning the breast with ultrasound in a state in which the breast is pressed by the pressing plate at a second pressure that is different from the first pressure, and scanning the upper face of the pressing plate with the ultrasound probe; and
finding an amount of change between a corresponding point of the first ultrasound image and a corresponding point of the second ultrasound image, and deriving information indicating a hardness of tissue of the breast based on the amount of change at the corresponding points and based on the first and second pressures.

15. A non-transitory storage medium storing a program that causes a computer to execute hardness deriving processing, the hardness deriving processing comprising:
acquiring a first ultrasound image from an ultrasound imaging device that performs ultrasound imaging of a breast by scanning the breast with ultrasound in a state in which the breast is pressed by a pressing plate at a first pressure and by scanning an upper face of the pressing plate with an ultrasound probe, and a second ultrasound image by moving the pressing plate, scanning the breast with ultrasound in a state in which the breast is pressed by the pressing plate at a second pressure that is different from the first pressure, and scanning the upper face of the pressing plate with the ultrasound probe; and
finding an amount of change between a corresponding point of the first ultrasound image and a corresponding point of the second ultrasound image, and deriving information indicating a hardness of tissue of the breast based on the amount of change at the corresponding points and based on the first and second pressures.

* * * * *